(12) United States Patent
Gerst et al.

(10) Patent No.: US 11,781,687 B2
(45) Date of Patent: Oct. 10, 2023

(54) SINGLE-USE GENDERLESS ASEPTIC FLUID COUPLINGS

(71) Applicant: Colder Products Company, St. Paul, MN (US)

(72) Inventors: Patrick T. Gerst, Oakdale, MN (US); Krista A. Vangsgard, Oakdale, MN (US); Michael J. Maleski, Coon Rapids, MN (US); Randall S. Williams, Minneapolis, MN (US)

(73) Assignee: Colder Products Company, Roseville, MN (US)

( * ) Notice: Subject to any disclaimer, the term of this patent is extended or adjusted under 35 U.S.C. 154(b) by 356 days.

(21) Appl. No.: 16/895,919

(22) Filed: Jun. 8, 2020

(65) Prior Publication Data
US 2021/0062946 A1   Mar. 4, 2021

Related U.S. Application Data

(60) Provisional application No. 62/948,607, filed on Dec. 16, 2019, provisional application No. 62/892,491, filed on Aug. 27, 2019.

(51) Int. Cl.
*F16L 33/035* (2006.01)
*A61M 39/10* (2006.01)
*F16L 55/105* (2006.01)
*F16L 37/084* (2006.01)

(52) U.S. Cl.
CPC ............ *F16L 33/035* (2013.01); *F16L 37/084* (2013.01); *F16L 55/105* (2013.01); *A61M 39/1011* (2013.01); *F16L 2201/44* (2013.01)

(58) Field of Classification Search
CPC ..... F16L 33/035; F16L 55/105; F16L 37/084; F16L 37/26; F16L 2201/44; A61M 39/16; A61M 39/18; A61M 39/165
See application file for complete search history.

(56) References Cited

U.S. PATENT DOCUMENTS

| | | |
|---|---|---|
| 913,144 A | 2/1909 | James et al. |
| 1,947,593 A | 2/1934 | Hamilton |
| 2,419,702 A | 4/1947 | Barnes |
| 2,868,563 A | 1/1959 | Wood |

(Continued)

FOREIGN PATENT DOCUMENTS

| | | |
|---|---|---|
| AU | 734259 | 6/2001 |
| CN | 1115965 | 1/1996 |

(Continued)

OTHER PUBLICATIONS

International Report on Patentability in International Application No. PCT/US2020/036673, dated Mar. 10, 2022, 8 pages.

(Continued)

*Primary Examiner* — Zachary T Dragicevich
*Assistant Examiner* — James A Linford
(74) *Attorney, Agent, or Firm* — Fish & Richardson P.C.

(57) ABSTRACT

Some fluid coupling devices described herein are configured for use in fluid systems. For example, some embodiments described in this document are single-use, aseptic fluid coupling devices that can be coupled to create a sterile flow path therethrough. Some such aseptic couplings are genderless couplings such that two identical aseptic couplings can be coupled together.

13 Claims, 34 Drawing Sheets

(56) References Cited

U.S. PATENT DOCUMENTS

| | | | |
|---|---|---|---|
| 3,391,951 A | 7/1968 | Miller | |
| 3,466,065 A | 9/1969 | Acker et al. | |
| 3,758,137 A | 9/1973 | Kershaw | |
| 3,831,984 A | 8/1974 | Kutina et al. | |
| 3,865,411 A | 2/1975 | Rowe et al. | |
| 3,900,223 A | 8/1975 | Schafer | |
| 3,909,910 A | 10/1975 | Rowe et al. | |
| 4,019,512 A | 4/1977 | Tenczar | |
| 4,022,205 A | 5/1977 | Tenczar | |
| 4,022,496 A | 5/1977 | Crissy | |
| 4,030,494 A | 6/1977 | Tenczar | |
| 4,187,846 A | 2/1980 | Lolachi et al. | |
| 4,418,945 A | 12/1983 | Kellogg | |
| 4,610,469 A | 9/1986 | Wolff-Mooij | |
| 4,621,841 A | 11/1986 | Wakefield | |
| 4,673,400 A | 6/1987 | Martin | |
| 4,738,401 A | 4/1988 | Fillcicchia | |
| 4,886,303 A | 12/1989 | Carson et al. | |
| 4,951,326 A | 8/1990 | Barnes et al. | |
| 5,316,351 A | 5/1994 | Czimny et al. | |
| 5,348,570 A | 9/1994 | Ruppert et al. | |
| 5,492,147 A | 2/1996 | Chailender | |
| 5,494,074 A | 2/1996 | Ramacier | |
| 5,810,398 A | 9/1998 | Matkovich | |
| 6,050,613 A | 4/2000 | Wartluft | |
| 6,655,655 B1 | 12/2003 | Matkovich et al. | |
| 6,679,529 B2 | 1/2004 | Johnson et al. | |
| 6,911,025 B2 | 6/2005 | Miyahara | |
| 7,083,605 B2 | 8/2006 | Miyahara | |
| 7,252,308 B2 | 8/2007 | Thilly | |
| 7,523,918 B2 | 4/2009 | Matkovich et al. | |
| 7,628,772 B2 | 12/2009 | McConnell et al. | |
| 7,628,782 B2 | 12/2009 | Adair et al. | |
| 7,918,243 B2 | 4/2011 | Diodati et al. | |
| 8,322,754 B2 | 12/2012 | Carcagno et al. | |
| 8,491,016 B2 | 7/2013 | Williams et al. | |
| 8,586,045 B2 | 11/2013 | Zeller et al. | |
| 9,364,653 B2 | 6/2016 | Williams et al. | |
| 9,879,808 B2 | 1/2018 | Williams et al. | |
| 10,267,443 B2 | 4/2019 | Blake | |
| 2002/0093192 A1 | 7/2002 | Matkovich | |
| 2003/0030272 A1 | 2/2003 | Johnson et al. | |
| 2003/0159764 A1 | 3/2003 | Goto | |
| 2004/0168690 A1 | 9/2004 | Payne | |
| 2006/0138069 A1 | 6/2006 | Domkowski et al. | |
| 2006/0192165 A1 | 8/2006 | Matkovich et al. | |
| 2006/0252298 A1 | 11/2006 | Biddel et al. | |
| 2007/0001459 A1 | 1/2007 | Wells | |
| 2007/0027437 A1 | 2/2007 | Burg et al. | |
| 2008/0067807 A1 | 3/2008 | deCler et al. | |
| 2009/0050213 A1 | 2/2009 | Biddel et al. | |
| 2009/0232586 A1 | 9/2009 | Diodati et al. | |
| 2009/0275888 A1 | 11/2009 | Kriesel | |
| 2010/0230950 A1 | 9/2010 | Williams et al. | |
| 2010/0230961 A1* | 9/2010 | Johnson | F16L 37/0985 285/352 |
| 2010/0292673 A1 | 11/2010 | Korogi et al. | |
| 2011/0061761 A1 | 3/2011 | Muehlemann | |
| 2013/0048111 A1 | 2/2013 | Gebauer | |
| 2013/0197485 A1 | 8/2013 | Gardner et al. | |
| 2013/0200607 A1 | 8/2013 | Rodenberg et al. | |
| 2013/0207380 A1* | 8/2013 | Williams | F16L 19/05 29/426.1 |
| 2013/0289517 A1 | 10/2013 | Williams et al. | |
| 2014/0358115 A1 | 12/2014 | Chelak et al. | |
| 2015/0028586 A1* | 1/2015 | Gerst | A61M 39/1011 285/352 |
| 2015/0314120 A1 | 11/2015 | Gardner | |
| 2016/0053927 A1 | 2/2016 | Whitaker | |
| 2016/0186906 A1* | 6/2016 | Blake | A61M 39/1011 285/319 |
| 2017/0284564 A1 | 10/2017 | Guymon | |
| 2017/0284584 A1 | 10/2017 | Kesselaar et al. | |
| 2018/0264251 A1 | 9/2018 | Lofving | |
| 2018/0304067 A1 | 10/2018 | Ryan | |
| 2019/0167971 A1 | 6/2019 | Shevitz | |

FOREIGN PATENT DOCUMENTS

| | | | |
|---|---|---|---|
| CN | 101132828 | 2/2008 | |
| CN | 102405369 | 4/2012 | |
| CN | 109999333 | 7/2019 | |
| EP | 2428718 | 3/2012 | |
| EP | 3359242 | 8/2018 | |
| JP | 2017505408 | 2/2017 | |
| WO | WO 2006/117138 | 11/2006 | |
| WO | WO 2010/118099 | 10/2010 | |
| WO | WO-2017210161 A1 * | 12/2017 | A61M 39/10 |

OTHER PUBLICATIONS

International Search Report and Written Opinion in International Application No. PCT/US20/36673, dated Oct. 22, 2020, 10 pages.

International Report on Patentability in International Application No. PCT/US2013/031418, dated Oct. 28, 2014, 5 pages.

International Search Report & Written Opinion in International Application No. PCT/US2013/026374, dated Jul. 8, 2013, 11 pages.

International Search Report and Written Opinion in International Application No. PCT/US2013/031418, dated May 23, 2013, 8 pages.

International Search Report and Written Opinion in International Application No. PCT/US2014/047413 dated Sep. 22, 2014, 11 pages.

International Search Report and Written Report in International Application No. PCT/US/2010/027311, dated Aug. 6, 2010 13 pages.

Invitation to Pay Additional Fees in International Application No. PCT/US20/36673, dated Aug. 18, 2020, 2 pages.

U.S. Appl. No. 14/336,178, filed Jul. 21, 2014 entitled "Aseptic Coupling Devices" (specification, claims, abstract, and drawings), 63 pages.

Extended European Search Report in European Appln No. 20856495.5, dated Sep. 13, 2022, 9 pages.

* cited by examiner

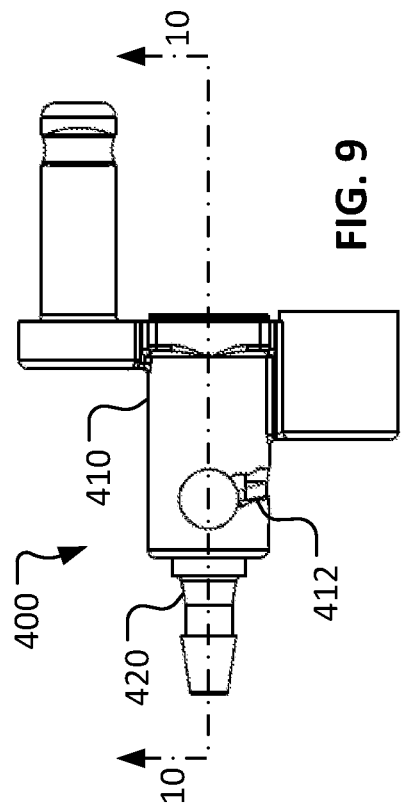
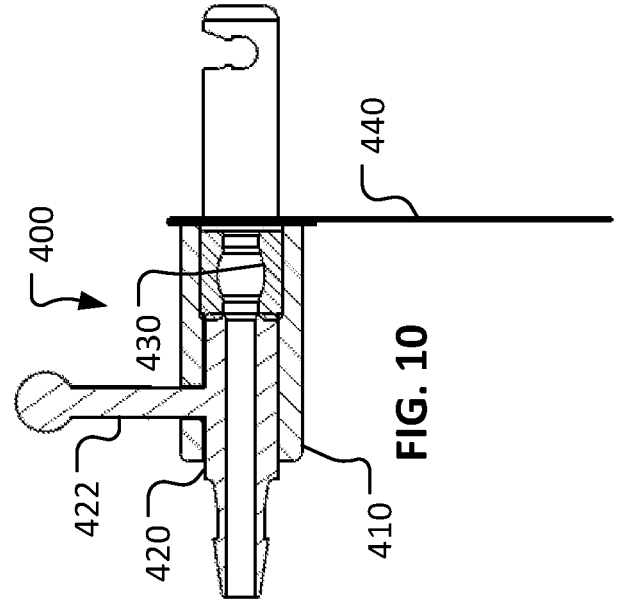
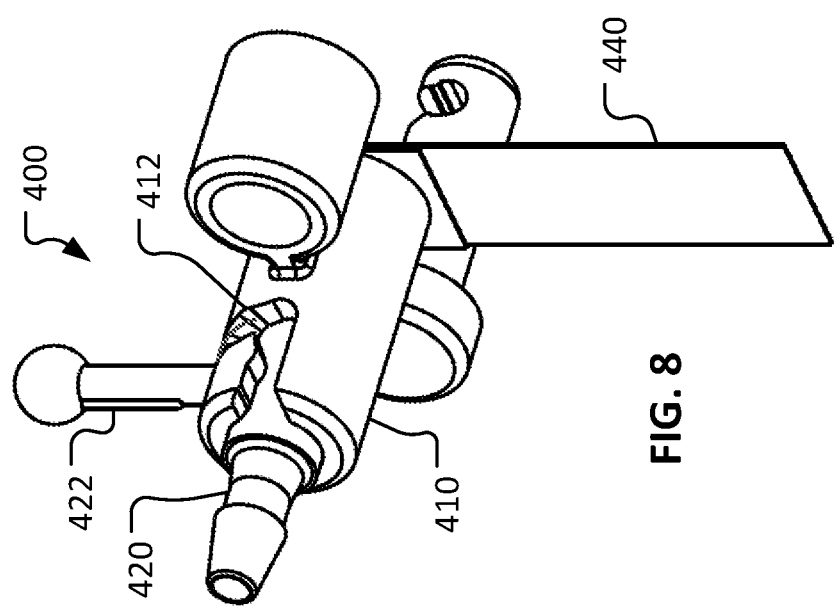
FIG. 8
FIG. 9
FIG. 10

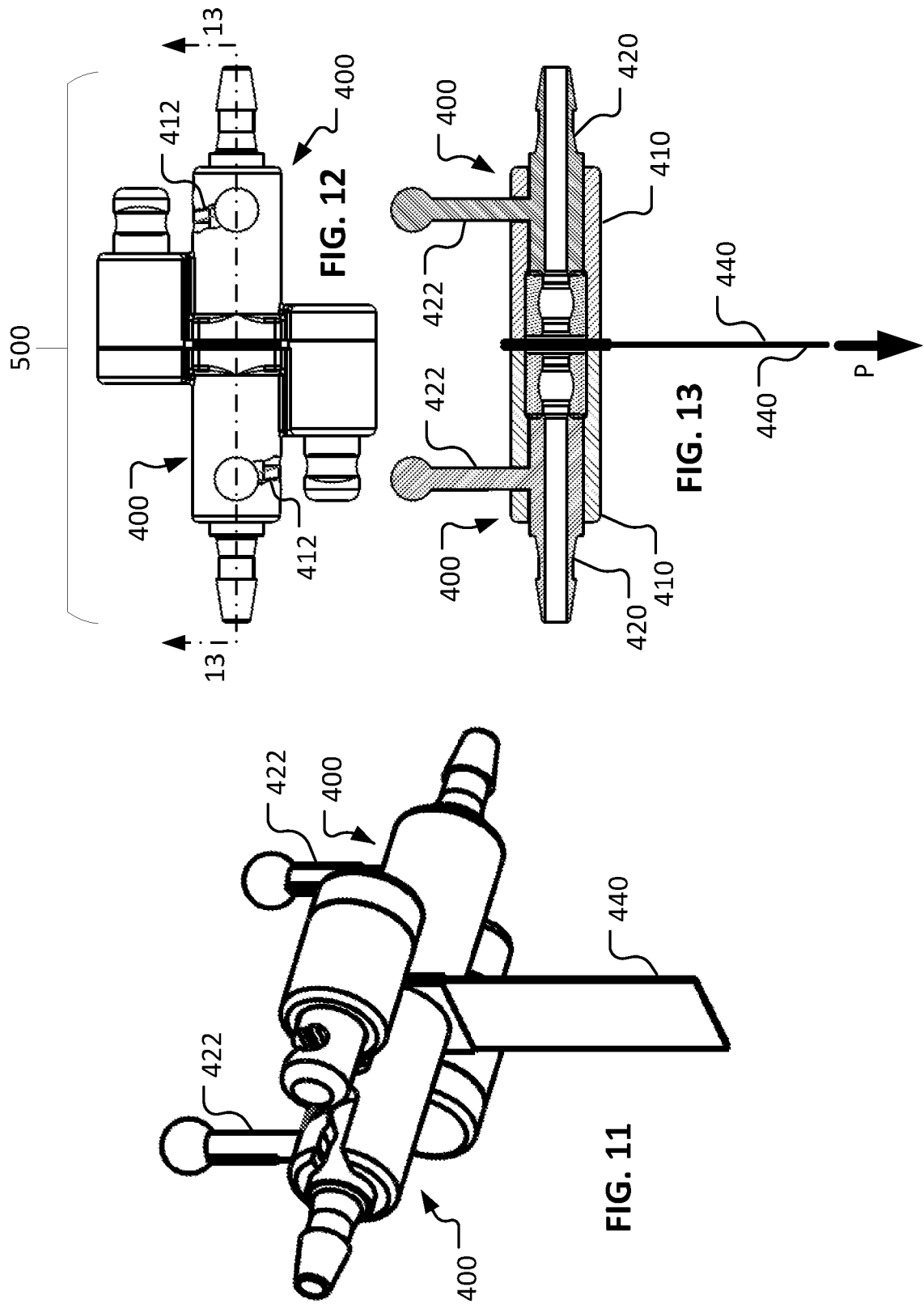

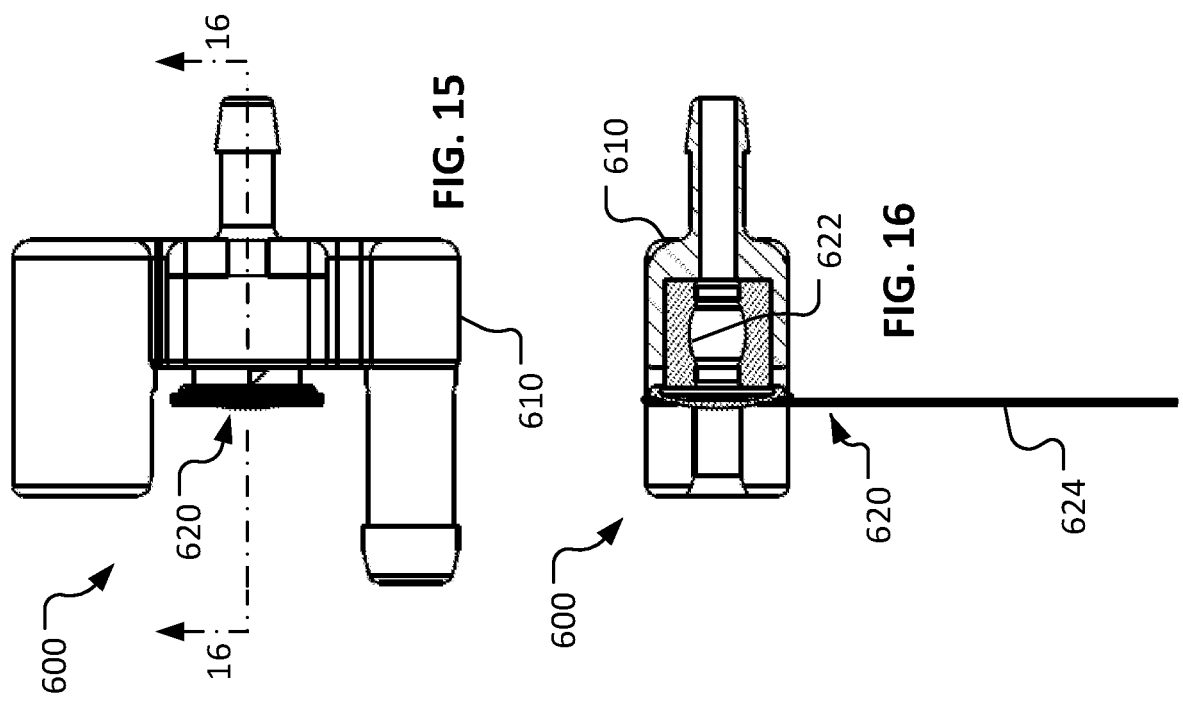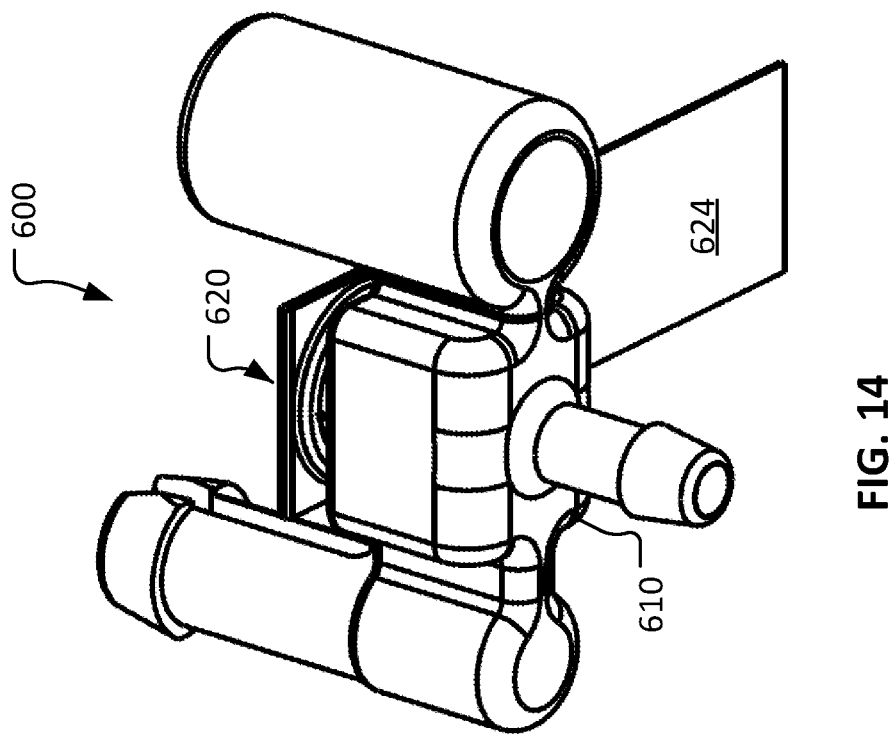

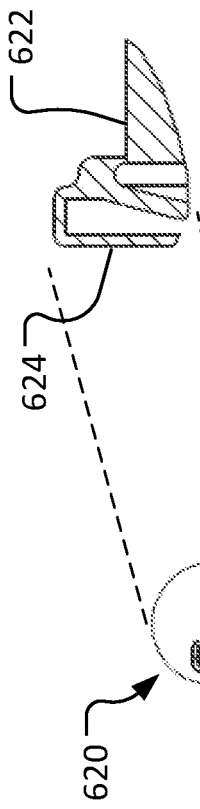
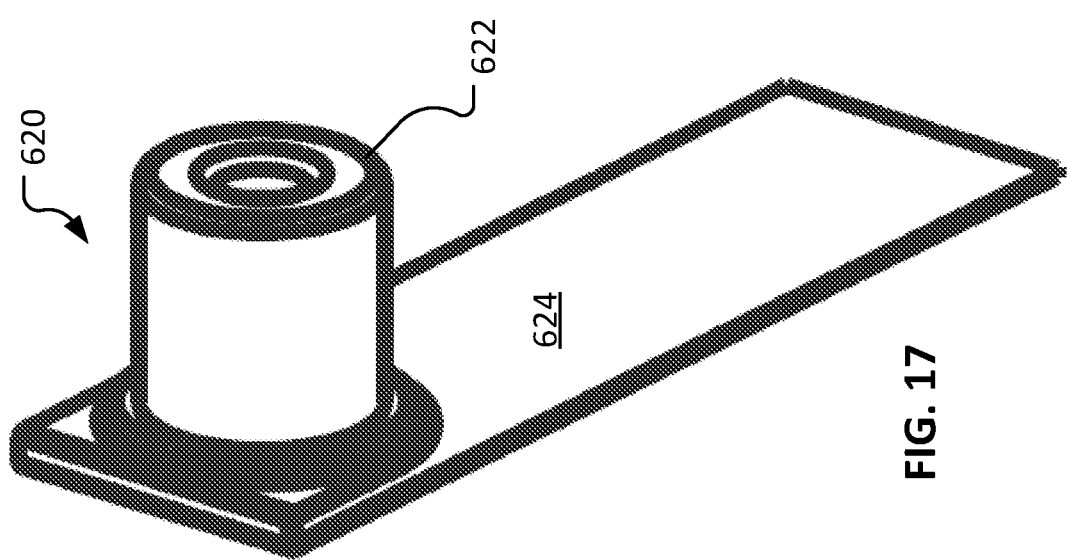
FIG. 19
FIG. 18
FIG. 17

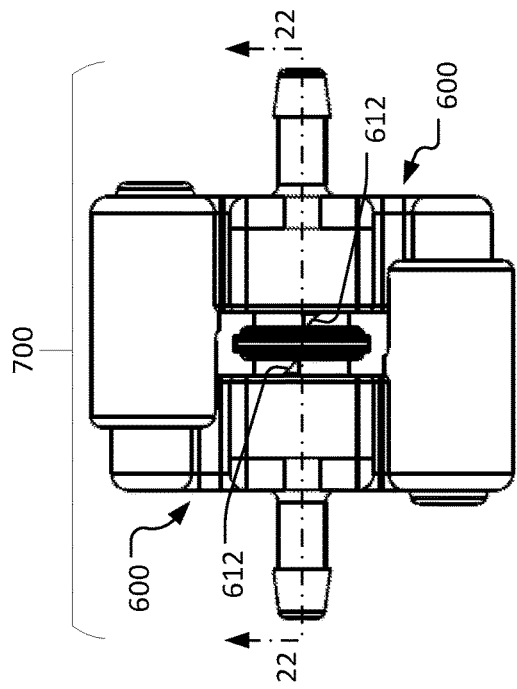
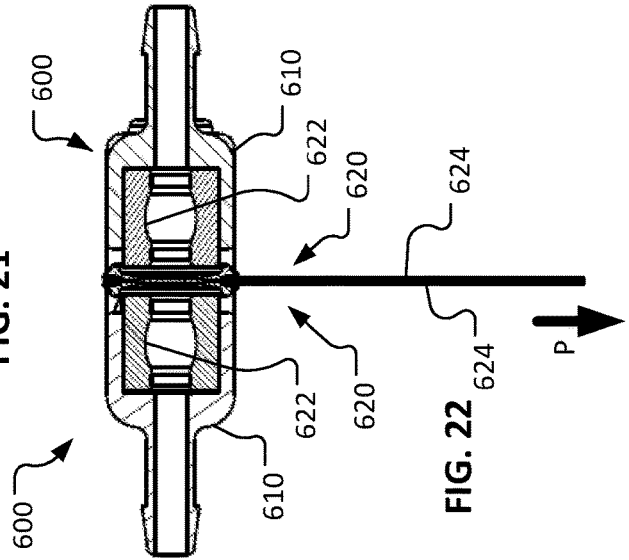
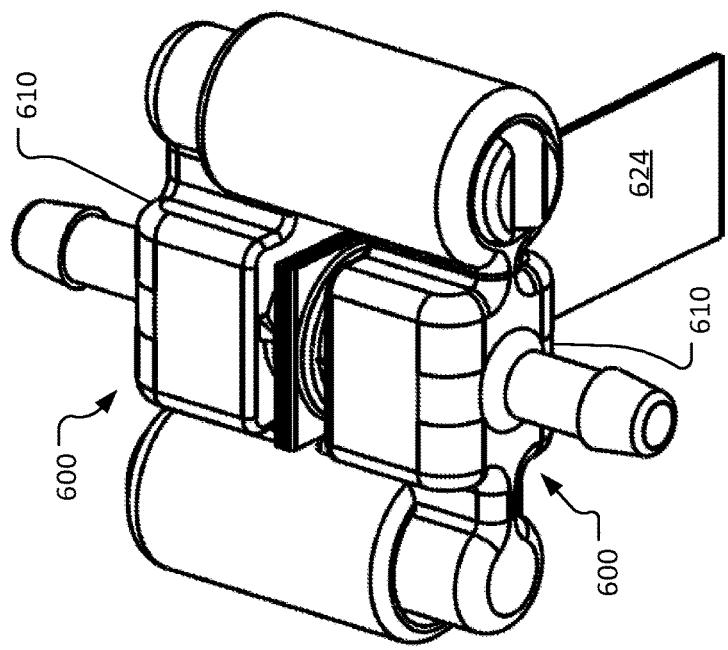

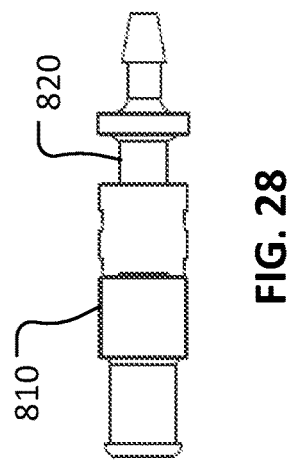
FIG. 28
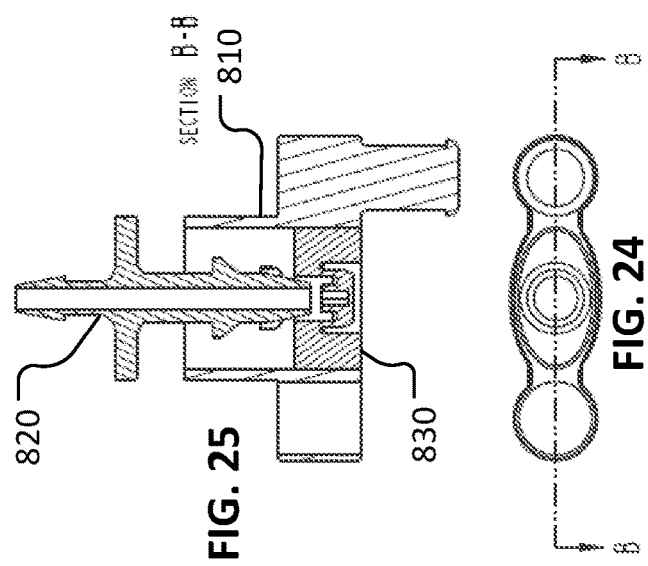
FIG. 25
FIG. 24
FIG. 26
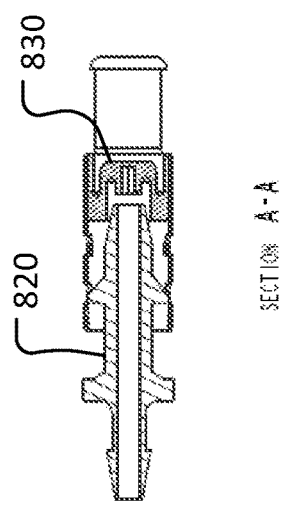
FIG. 27

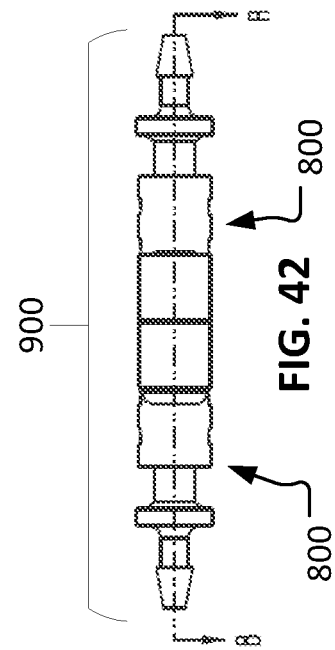
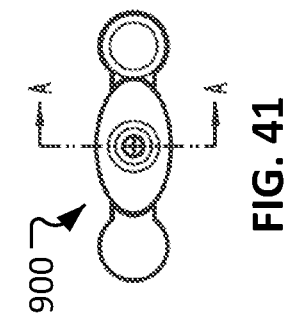
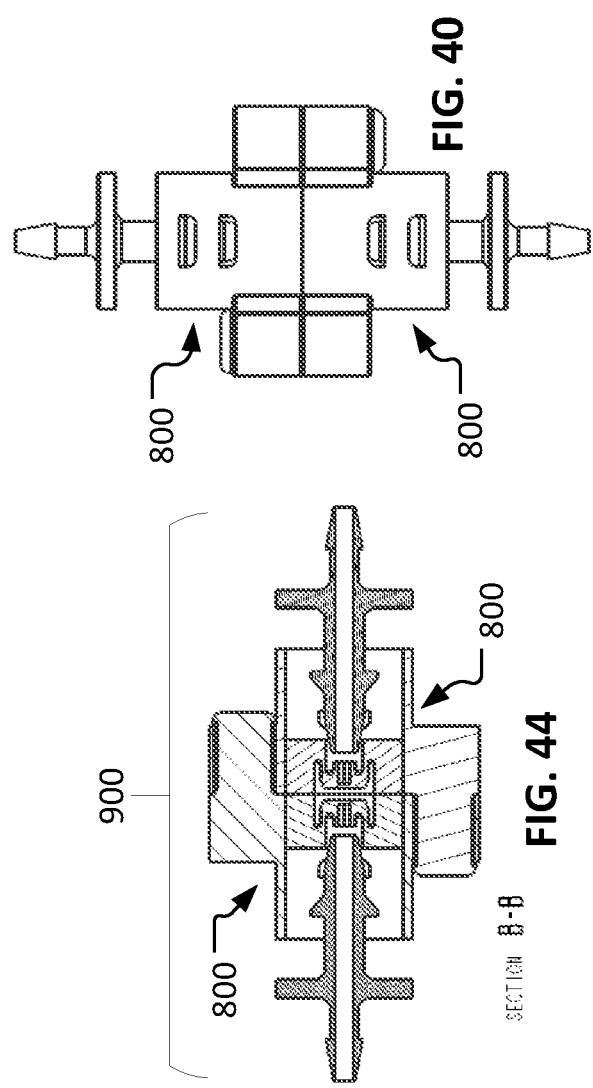
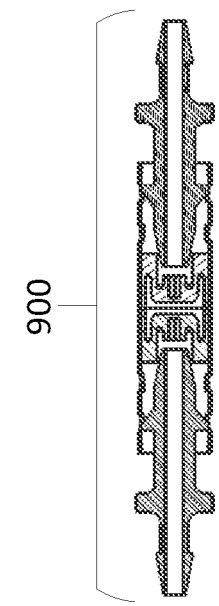
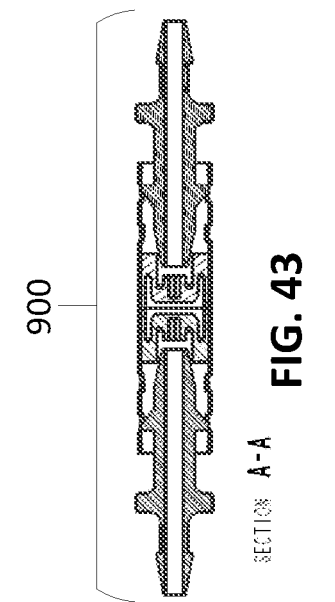

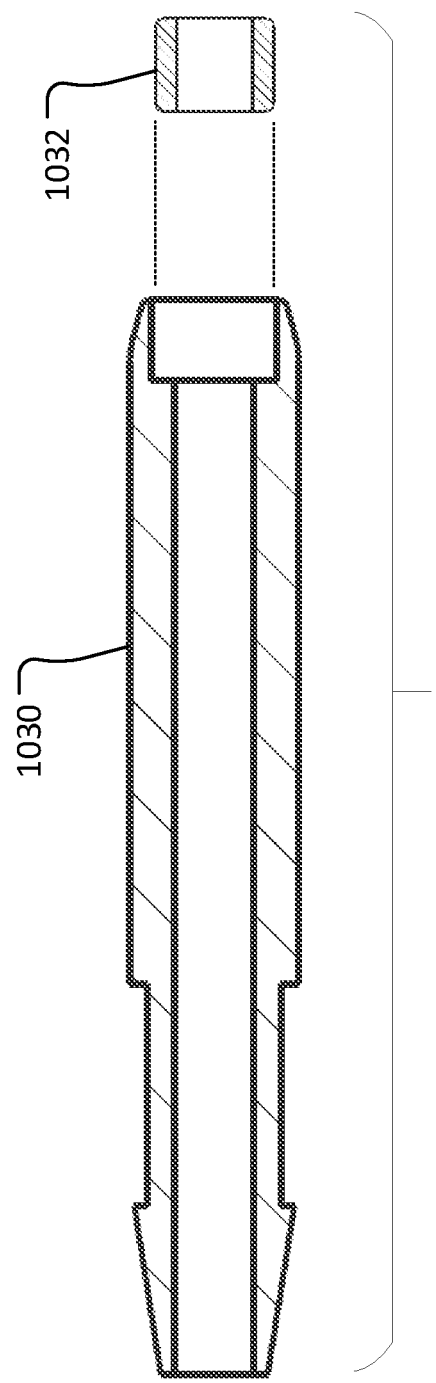

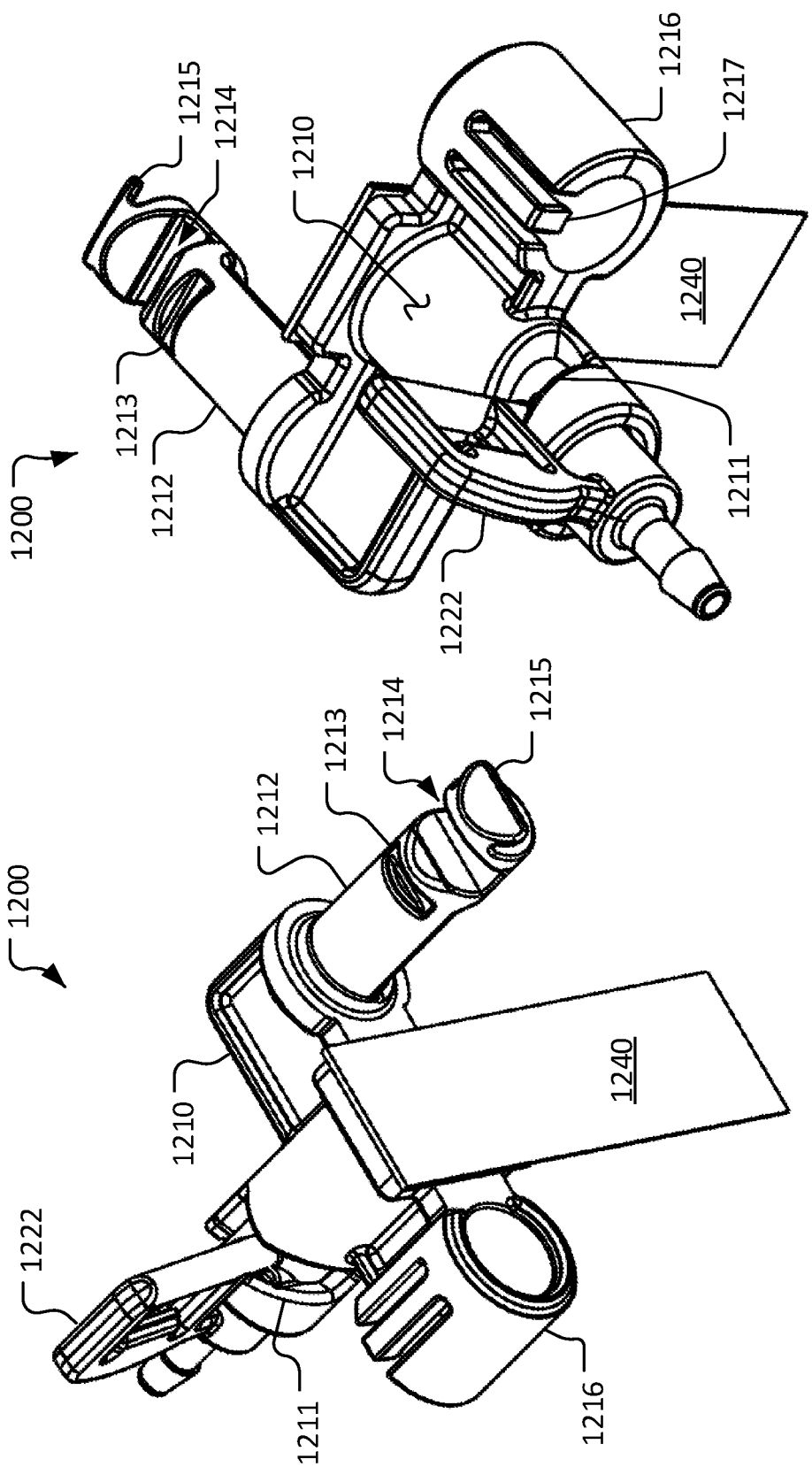

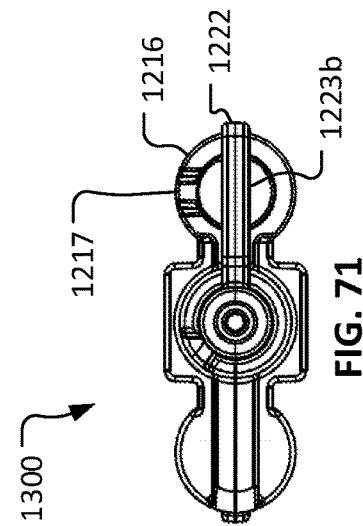
FIG. 71
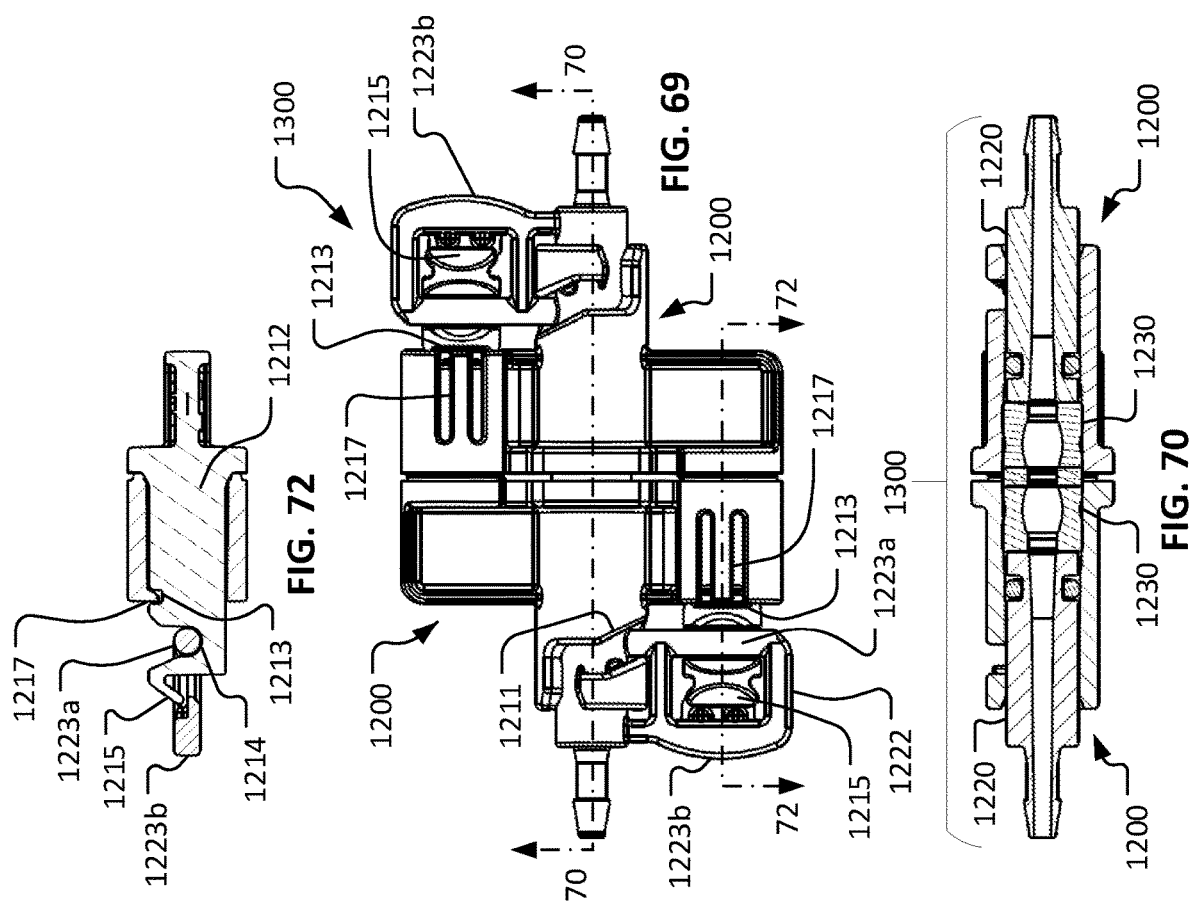
FIG. 72
FIG. 69
FIG. 70

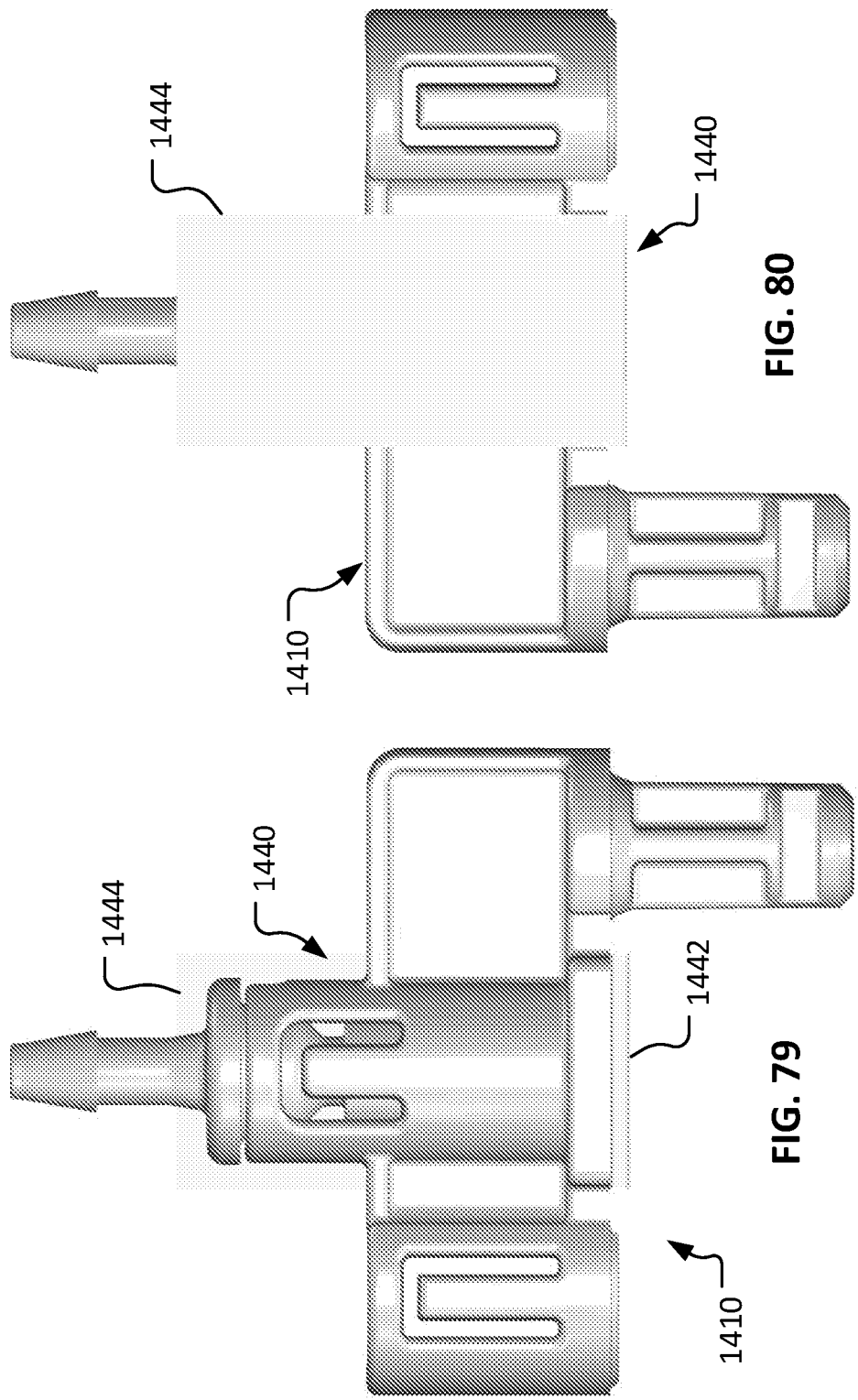

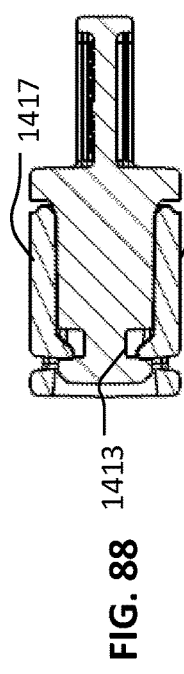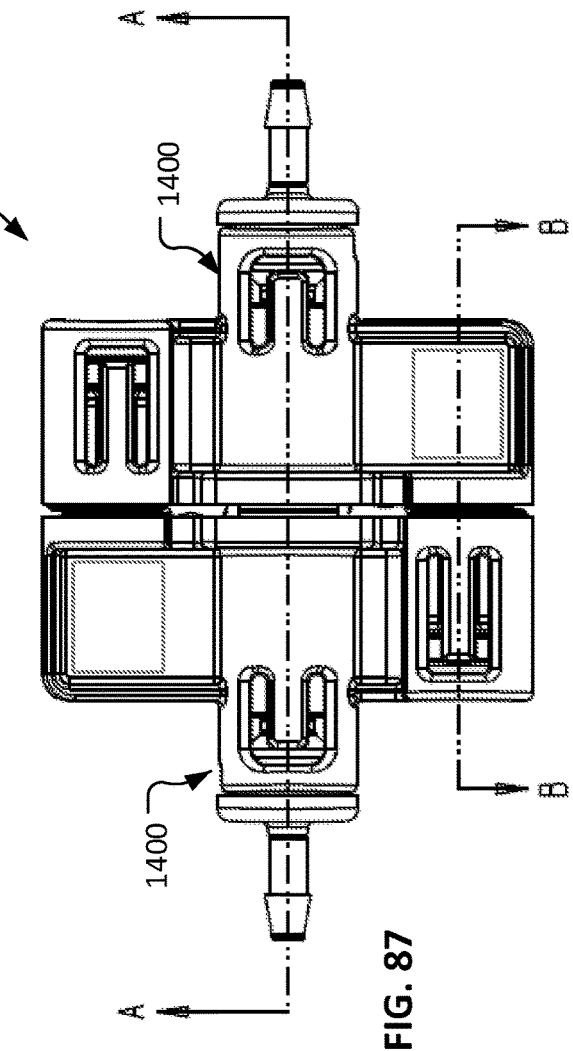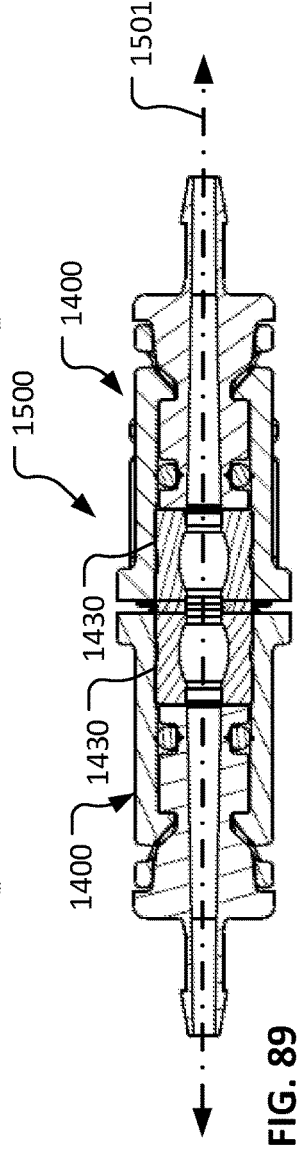

SINGLE-USE GENDERLESS ASEPTIC FLUID COUPLINGS

CROSS-REFERENCE TO RELATED APPLICATIONS

This application claims the benefit of U.S. Provisional Application Ser. No. 62/892,491, filed Aug. 27, 2019, and U.S. Provisional Application Ser. No. 62/948,607, filed Dec. 16, 2019. The disclosures of the prior applications are considered part of (and are incorporated by reference in) the disclosure of this application.

BACKGROUND

1. Technical Field

This document relates to fluid coupling devices for fluid systems and methods. For example, some embodiments described in this document relate to single-use, aseptic fluid coupling devices.

2. Background Information

Some fluid systems, such as some bioprocessing fluid systems or blood handling systems, may require fluid couplings that can aseptically connect a fluid flow path. In one example implementation, it is desirable to connect one or more sample bags to be able to receive a sample of fluid from a bioreactor system in a manner that prevents contamination of the fluid sample. In that scenario, an aseptic coupling can be used to connect the sample bag(s) to receive the fluid(s) from the bioreactor system while substantially preventing biological contamination of the fluid(s) from the coupling and the environment.

SUMMARY

This document describes a number of fluid coupling devices for fluid systems and methods. In some embodiments, the fluid coupling devices can be implemented as single-use, aseptic fluid coupling connection devices. In the context of this disclosure, the term "fluid" includes both gases and liquids.

In particular embodiments, the fluid coupling devices described herein are single-use devices because, after the two portions of the coupling (also referred to herein as "coupling halves" and/or "connectors") are connected to each other, the coupled portions are designed to resist uncoupling. For example, such single-use coupling devices are equipped with one or more mechanical components that operate like locks to maintain the two portions of the coupling in the coupled state. Hence, in these particular embodiments, the fluid coupling devices provided herein are structurally configured to be single-use connection devices so that, after the single-use coupling halves have been connected to each other, they cannot be operably disconnected from each other (as such, preserving the sterility or biological integrity of the system/flow path/etc.).

Additionally, in such single-use embodiments or in other embodiments, the fluid coupling devices can be configured as "aseptic" coupling devices in that can be connected to each other while inhibiting biological contamination from migrating into the flow paths. Such an "aseptic" coupling will also serve to limit the exposure of the fluid to the surrounding environment.

Further, in such single-use embodiments, or other embodiments, the fluid coupling devices can be configured as genderless couplings. That is, the two coupling portions can be designed exactly alike so that there is no male or female coupling halves as in many conventional fluid coupling designs.

In one aspect, this disclosure is directed to an aseptic fluid coupling and methods for use. In some embodiments, such an aseptic fluid coupling can include: (i) a main body defining a longitudinal axis, a bore, and a fluid flow path through the main body along the longitudinal axis; (ii) a seal member including a portion disposed within the bore and a portion extending from the front face around the longitudinal axis; and (iii) a flexible membrane including a portion attached to the front face around the seal member to block contaminants from entering the fluid flow path, the membrane also including a tail end portion that is at an opposite end of the membrane in comparison to the portion attached to the front face. The main body can include a front face; a termination that is at an opposite end of the main body in comparison to the front face; an alignment post; and an alignment guide defining internal space configured to slidably receive an alignment post of another aseptic fluid coupling when two of the aseptic fluid couplings are mated together.

Such an aseptic fluid coupling may optionally include one or more of the following features. The alignment post may extend parallel to the longitudinal axis. The membrane may be porous such that air can pass through the membrane. The alignment post and the alignment guide may each include attachment features whereby the alignment post latches with an engaged alignment guide and the alignment guide latches with an engaged alignment post. The attachment features of the alignment post may include at least one groove. The attachment features of the alignment guide may include at least one flexible latch member. The main body may include a termination member that includes the termination. The termination member may extend into the bore. The termination member may snap into engagement with other portions of the main body. The termination member may be rotatable about the longitudinal axis in relation to the other portions of the main body. The aseptic fluid coupling may also include a seal disposed between the termination member and the other portions of the main body. The termination member may define a portion of the fluid flow path. The termination member may abut against the seal member within the bore. The aseptic fluid coupling may also include a protective cover that is releasably engageable with the main body. The protective cover may press two layers of the membrane against the seal member while the protective cover is engaged with the main body. The protective cover may define an opening aligned with the longitudinal axis while the protective cover is engaged with the main body.

In another aspect, this disclosure is directed to an aseptic fluid coupling that includes a main body defining a longitudinal axis, a bore, and a fluid flow path through the main body along the longitudinal axis; a seal member including a portion extending from the front face; and a flexible membrane including a portion attached to the front face around the seal member. The main body includes a front face, an alignment post, and an alignment guide.

Such an aseptic fluid coupling may optionally include one or more of the following features. The alignment guide may define an internal space configured to slidably receive an alignment post of another aseptic fluid coupling when two of the aseptic fluid couplings are mated together. A centerline of the alignment post, a centerline of the alignment guide, and the longitudinal axis may all be in a same plane. The bore may be between the alignment post and the alignment guide. In some embodiments, a distance between the longitudinal axis and the centerline of the alignment post is equal to a distance between the longitudinal axis and the centerline of the alignment guide.

In another aspect, this disclosure is directed to an aseptic fluid coupling device that includes: a main body; a cover slidably attached to the main body; a first seal between the cover and the main body; a second seal within the main body; a seal pusher slidably coupled to the main body and positioned to abut against the second seal; and a lock ring threadedly coupled to the main body and rotatably coupled to the seal pusher.

In another aspect, this disclosure is directed to an aseptic fluid coupling device that includes: a main body defining a longitudinal axis; a seal within the main body; a seal pusher movably coupled to the main body and positioned to abut against the seal, the seal pusher comprising a seal pusher lever slidably coupled in a slot defined by the main body; and a membrane removably coupled to a front face of the main body. The slot defined by the main body extends at an acute angle relative to the longitudinal axis such that rotating the seal pusher relative to the main body pushes the seal along the longitudinal axis relative to the main body.

In another aspect, this disclosure is directed to an aseptic fluid coupling device that includes: a main body; and a seal disposed within the main body and having a pull tab unitarily formed therewith. The main body includes a piercing element positioned to pierce a portion of the seal or pull tab.

In another aspect, this disclosure is directed to an aseptic fluid coupling device that includes: a main body at least a portion of which has an ovular cross-sectional shape; a seal disposed within the main body; and an insert slidably coupled to the main body and slidable along a longitudinal axis of the main body between a first position and a second position. Moving the insert from the first position to the second position causes the insert to pierce the seal.

In another aspect, this disclosure is directed to an aseptic fluid coupling device that includes: a seal body; a first seal within the seal body; a twist collar threadedly coupled to the seal body; and a plunger slidably coupled to the seal body and positioned to pierce the first seal in response to rotation of the twist collar in relation to the seal body. The plunger includes a second seal attached to a tip thereof.

In another aspect, this disclosure is directed to an aseptic fluid coupling device that includes: a main body defining a longitudinal axis; a seal within the main body; a seal pusher movably coupled to the main body and positioned to abut against the seal, the seal pusher comprising a seal pusher lever with two radially-extending portions slidably, the seal pusher lever slidably coupled in a slot defined by the main body; and a membrane removably coupled to a front face of the main body and covering the seal. The slot defined by the main body extends at an acute angle relative to the longitudinal axis such that rotating the seal pusher relative to the main body pushes the seal along the longitudinal axis relative to the main body.

Particular embodiments of the subject matter described in this document can be implemented to realize one or more of the following advantages. First, in some embodiments, the fluid coupling devices may advantageously provide a user with audible, visual, and/or tactile feedback in reference to the motions performed for physically connecting the two portions of the fluid coupling devices to each other. Such audible and/or tactile feedback can provide the user with an efficient and conclusive indication or confirmation of the proper function and desired configuration of the fluid coupling device.

Second, some embodiments of the fluid coupling devices provided herein are a metallic-free construction (also referred to as a nonmetallic fluid coupling device). As such, such embodiments of the nonmetallic fluid coupling devices can be advantageously sterilized using a gamma sterilization technique. Also, in some circumstances, the nonmetallic fluid coupling devices exhibit enhanced fatigue-resistance characteristics, minimal installed stress, and enhanced corrosion resistance in comparison to some fluid couplings that include traditional metallic parts such as metal springs.

Third, some embodiments of the fluid coupling devices provide an improved aseptic connection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the connection of particular fluid couplings in a sterile room or within a sterile flow-hood to prevent biological contamination.

Fourth, some embodiments of the fluid coupling devices provided herein are advantageously designed to be genderless. Accordingly, usage of the fluid coupling devices are simplified and a user may be able to carry less inventory of fluid coupling components. Also, the genderless aspect of the fluid couplings offers additional system flexibility because anything with one of these couplings can connect to anything else with another one of these couplings.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 8 is a perspective view of another example aseptic coupling in accordance with some embodiments.

FIG. 9 is a side view of the aseptic coupling of FIG. 8.

FIG. 10 is a longitudinal cross-sectional view of the aseptic coupling of FIG. 8 taken along break line 10-10 of FIG. 9.

FIG. 11 is a perspective view of two of the aseptic couplings of FIG. 8 in a pre-coupled configuration.

FIG. 12 is a side view of two of the aseptic couplings of FIG. 8 in a pre-coupled configuration.

FIG. 13 is a longitudinal cross-sectional view of two of the aseptic couplings of FIG. 8 in the pre-coupled configuration taken along break line 13-13 of FIG. 12.

FIG. 14 is a perspective view of another example aseptic coupling in accordance with some embodiments.

FIG. 15 is a side view of the aseptic coupling of FIG. 14.

FIG. 16 is a longitudinal cross-sectional view of the aseptic coupling of FIG. 14 taken along break line 15-15 of FIG. 15.

FIG. 17 is a perspective view of a seal and pull tab of the aseptic coupling of FIG. 14.

FIG. 18 is a cross-sectional view of the seal and pull-tab of FIG. 17.

FIG. 19 shows a portion of the cross-sectional view of the seal and pull-tab of FIG. 18.

FIG. 20 is a perspective view of two of the aseptic couplings of FIG. 14 in a pre-coupled configuration.

FIG. 21 is a side view of two of the aseptic couplings of FIG. 14 in the pre-coupled configuration.

FIG. 22 is a longitudinal cross-sectional view of two of the aseptic couplings of FIG. 14 taken along break line 22-22 of FIG. 21.

FIG. 24 is an end view of the aseptic coupling of FIG. 23.

FIG. 25 is a longitudinal cross-sectional view of the aseptic coupling of FIG. 23 taken along the break line B-B of FIG. 24.

FIG. 26 is a top view of the aseptic coupling of FIG. 23.

FIG. 27 is a longitudinal cross-sectional view of the aseptic coupling of FIG. 23 taken along the break line A-A of FIG. 26.

FIG. 28 is a side view of the aseptic coupling of FIG. 23.

FIG. 40 is a side view of two of the aseptic couplings of FIG. 23 in a pre-coupled configuration.

FIG. 41 is an end view of two of the aseptic couplings of FIG. 23 in the pre-coupled configuration.

FIG. 42 is another side view of two of the aseptic couplings of FIG. 23 in the pre-coupled configuration.

FIG. 43 is a longitudinal cross-section of two of the aseptic couplings of FIG. 23 in the pre-coupled configuration taken along the break line A-A of FIG. 41.

FIG. 44 is a longitudinal cross-section of two of the aseptic couplings of FIG. 23 in the pre-coupled configuration taken along the break line B-B of FIG. 42.

FIG. 51 is an exploded longitudinal cross-sectional view of a plunger component and seal of the aseptic coupling of FIG. 45.

FIG. 64 is a perspective view of the aseptic coupling of FIG. 61.

FIG. 65 is another perspective view of the aseptic coupling of FIG. 61.

FIG. 69 is a top view of two of the aseptic couplings of FIG. 61 in a coupled configuration.

FIG. 70 is a longitudinal cross-sectional view of two coupled aseptic couplings of FIG. 61 taken along break line 70-70 of FIG. 69.

FIG. 71 is an end view of two of the aseptic couplings of FIG. 61 in a coupled configuration.

FIG. 72 is a longitudinal cross-sectional view of two coupled aseptic couplings of FIG. 61 taken along break line 72-72 of FIG. 69.

FIG. 79 is a top view of the aseptic coupling of FIG. 73 without its protective cover.

FIG. 80 is a bottom view of the aseptic coupling of FIG. 73 without its protective cover.

FIG. 87 is a top view showing two of the aseptic couplings of FIG. 73 in a coupled arrangement.

FIG. 88 is a longitudinal cross-sectional view taken along break line B-B of FIG. 87.

FIG. 89 is a longitudinal cross-sectional view taken along break line A-A of FIG. 87.

Like reference numbers represent corresponding parts throughout.

DETAILED DESCRIPTION OF ILLUSTRATIVE EMBODIMENTS

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

As used herein, the term "aseptic" refers to any process that maintains a sterilized surface or volume.

As used herein, the term "fluid" means any substance that can be made to flow including, but is not limited to, liquids, gases, granular or powdered solids, mixtures or emulsions of two or more fluids, suspensions of solids within liquids or gases, etc.

Figure 1:
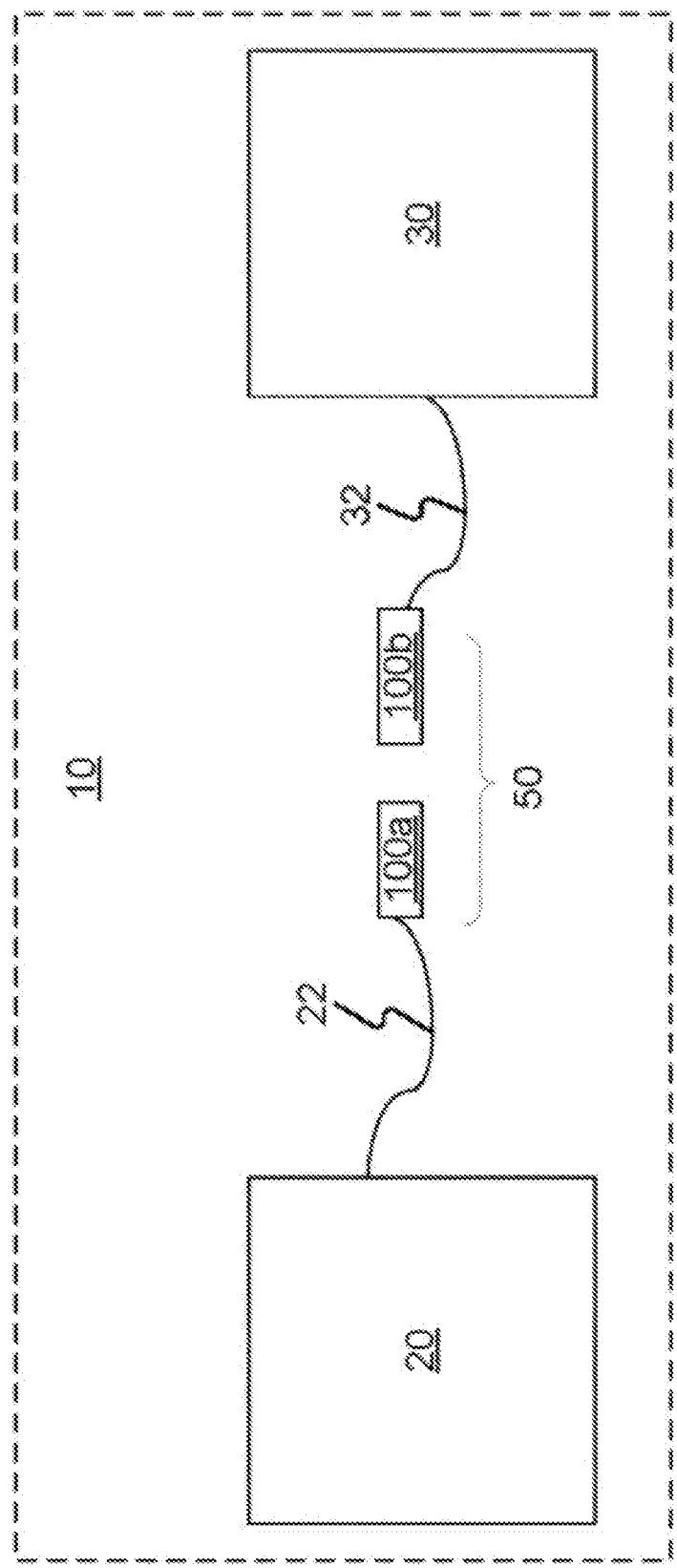
FIG. 1 is a schematic view of an example fluid system including an example fluid coupling arranged in a pre-connected configuration, in accordance with some embodiments provided herein.
Figure 3:
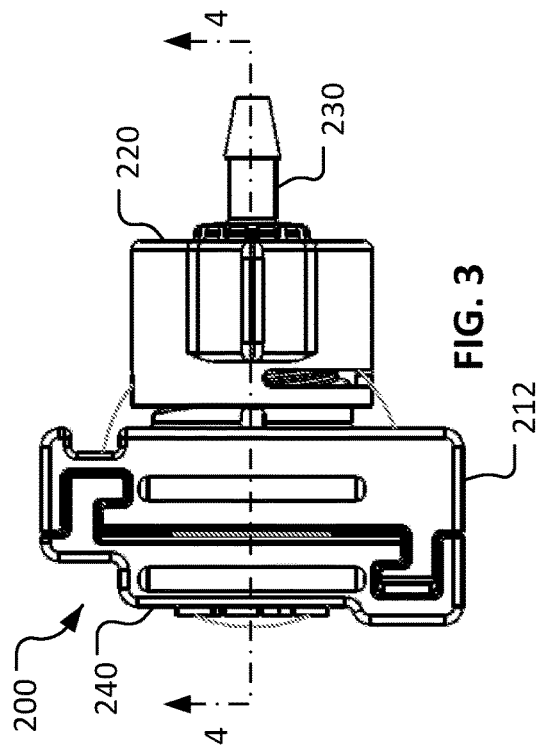
FIG. 3 is a top view of the aseptic coupling of FIG. 2.
Figure 4:
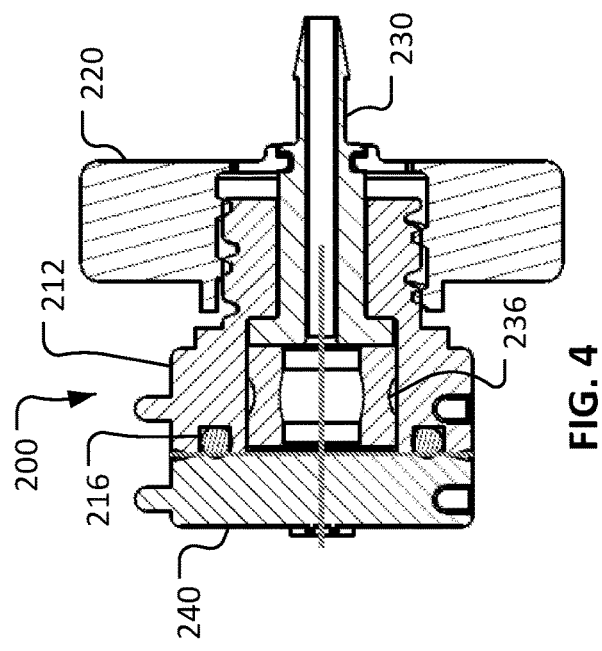
FIG. 4 is a longitudinal cross-sectional view of the aseptic coupling of FIG. 2 taken along break line 4-4 of FIG. 3.
Figure 2:
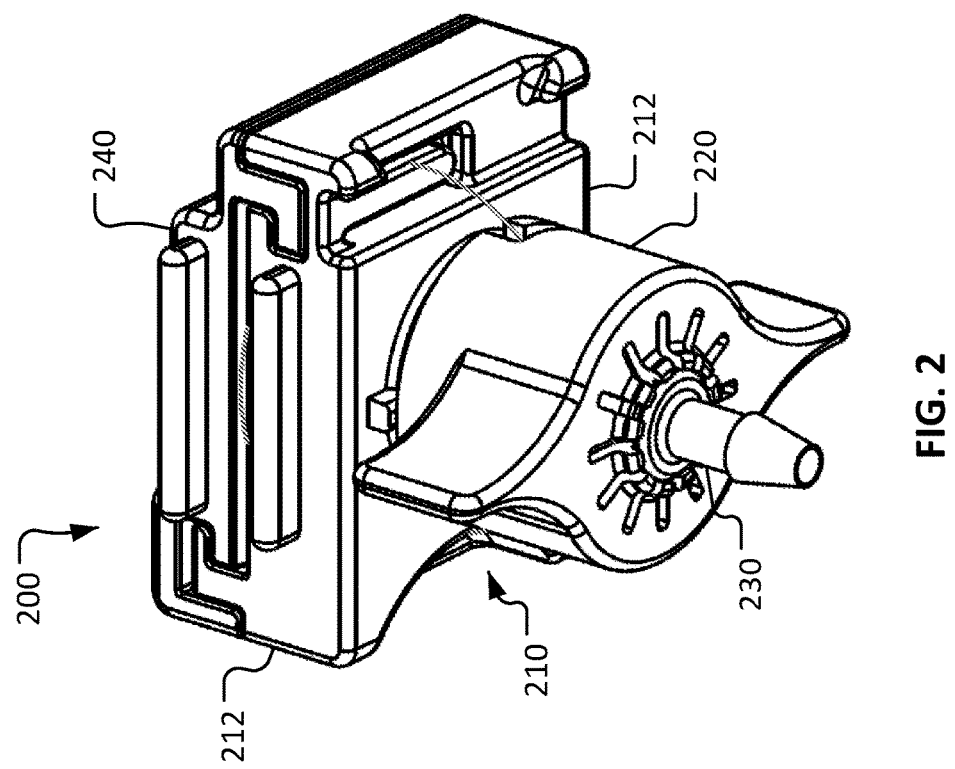
FIG. 2 is a perspective view of an example aseptic coupling in accordance with some embodiments.

Referring now to FIG. 1, an example system 10 is shown. System 10 includes a first piece of processing equipment 20 and a second piece of processing equipment 30. In example embodiments, equipment 20 and 30 are bioreactors including biomaterial. In other embodiments, equipment 20 and 30 can be other apparatuses that require a sterile connection therebetween such as, for example, a bioreactor and a media bag, sample bag, or other receptacle.

Equipment 20 includes a fluid pathway 22 extending therefrom that is terminated by an aseptic coupling arrangement 50 including a first aseptic coupling device 100a. Likewise, equipment 30 includes a fluid pathway 32 extending therefrom that is terminated by a second aseptic coupling device 100b of the aseptic coupling arrangement 50. The coupling arrangement 50 is representative of the multiple different aseptic couplings described herein.

In example embodiments, aseptic coupling devices 100a and 100b are substantially similar or genderless (e.g., identical except for possibly differences in terminations). However, it is noted that each aseptic coupling device 100a, 100b may be provided with different features than the other, as desired.

In example embodiments, the fluid containing environments within pathways 22 and 32 and aseptic coupling devices 100a and 100a are sterile. In some embodiments, the aseptic coupling arrangement 50 can be placed in an uncoupled configuration, one or more pre-coupled configurations, and in a coupled configuration, as described further below. In a pre-coupled configuration, while the coupling devices are mechanically coupled to each other, no fluid flow path is open therethrough.

The coupling devices 100a and 100a are designed and configured so that they can be reconfigured from the uncoupled state to the coupled state (e.g., to connect pathways 22 and 32) while preventing a loss of sterility of the fluid containing environments within the pathways 22 and 32. Hence, using the aseptic coupling arrangement 50, fluid can be transferred between equipment 20 and 30 (via coupling devices 100a and 100a) without becoming biocontaminated.

Figure 6:
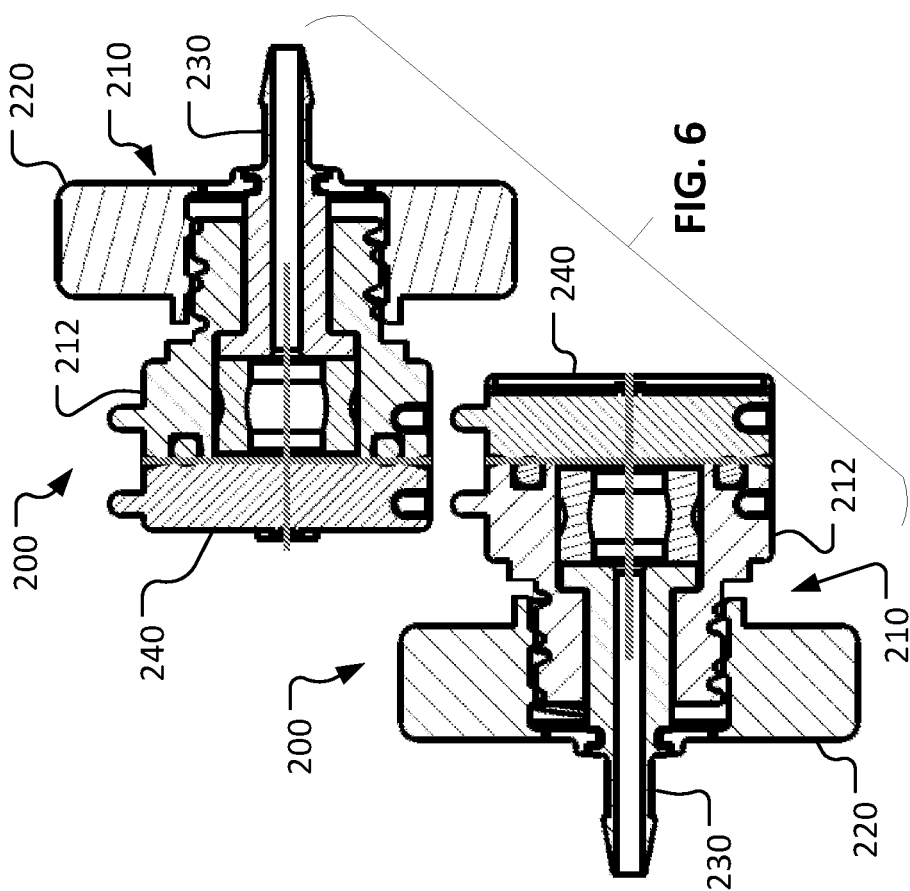
FIG. 6 shows a longitudinal cross-sectional view of two of the aseptic couplings of FIG. 2 in an uncoupled configuration.
Figure 7:
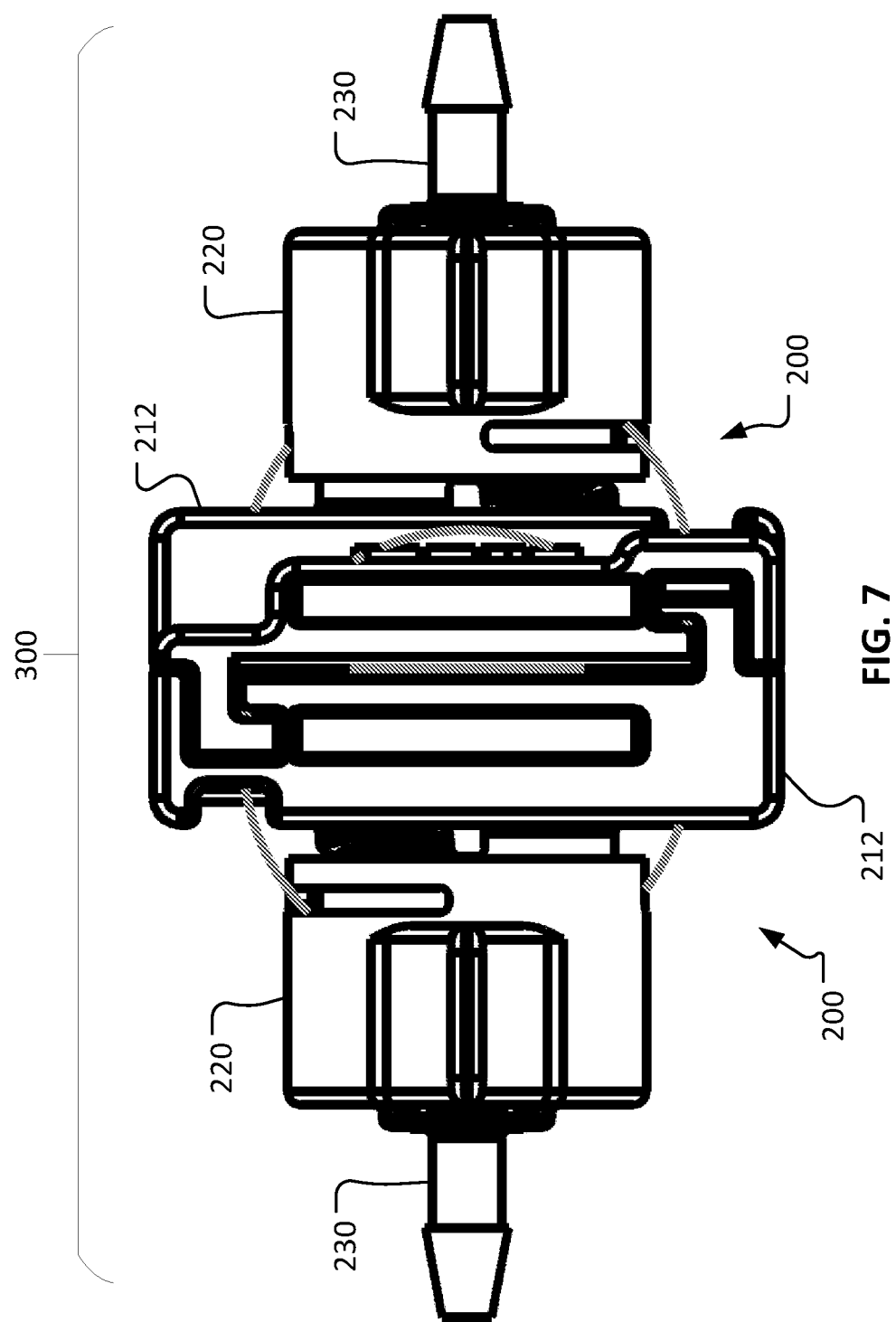
FIG. 7 is a side view of two of the aseptic couplings of FIG. 2 in a pre-coupled configuration.
Figure 23:
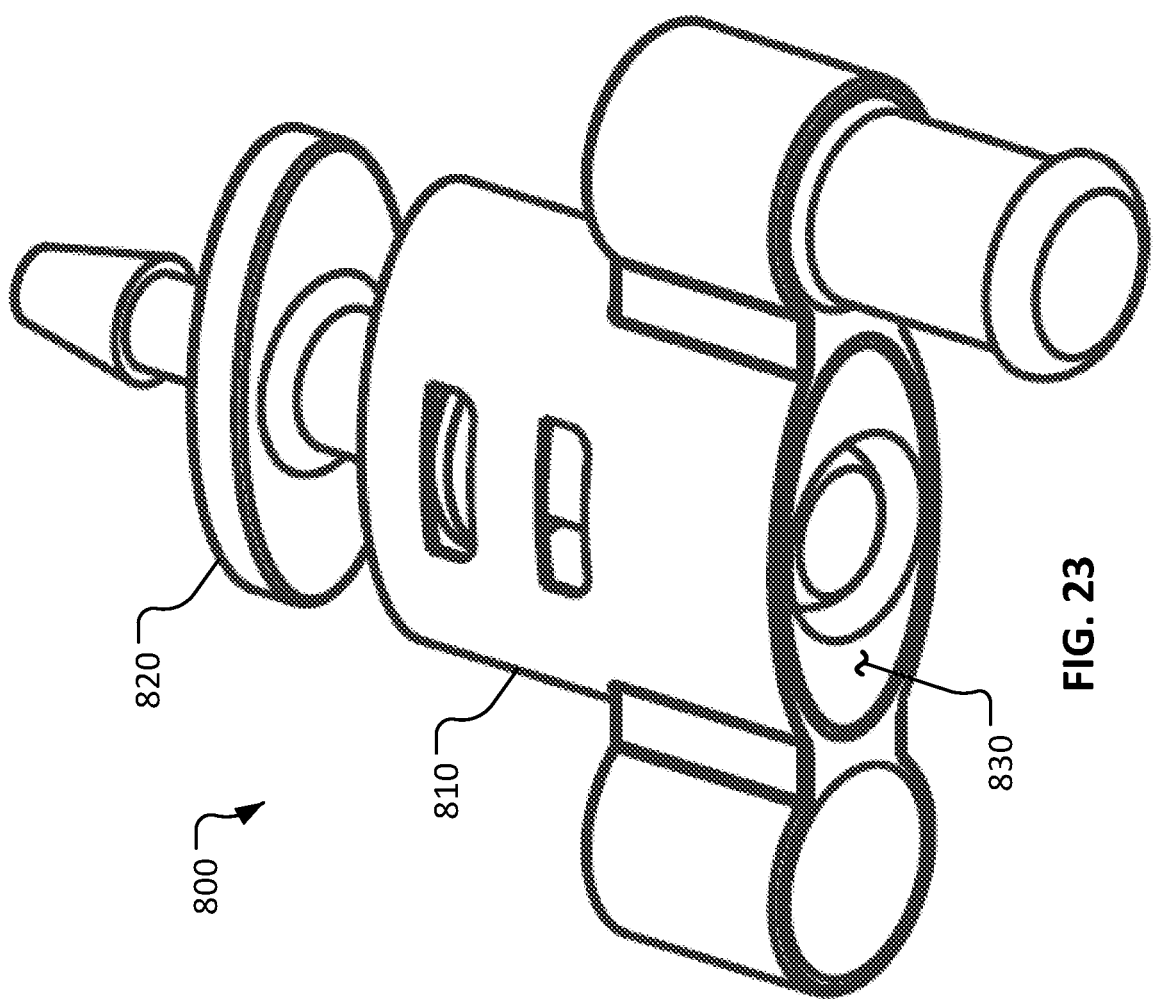
FIG. 23 is a perspective view of another example aseptic coupling in accordance with some embodiments.
Figure 29:
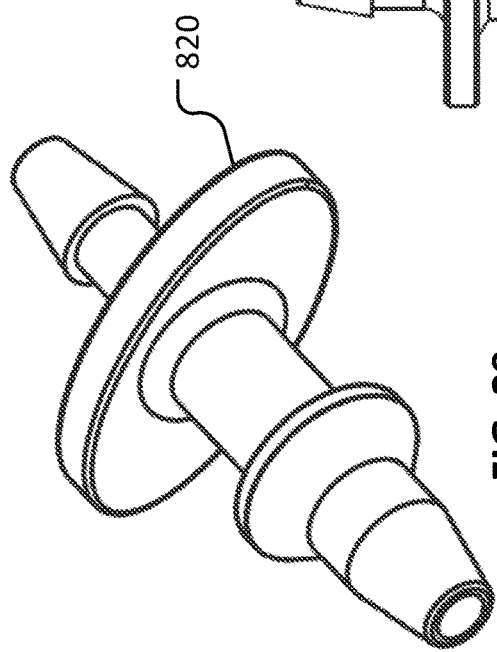
FIG. 29 is a perspective view of an insert component of the aseptic coupling of FIG. 23.
Figure 32:
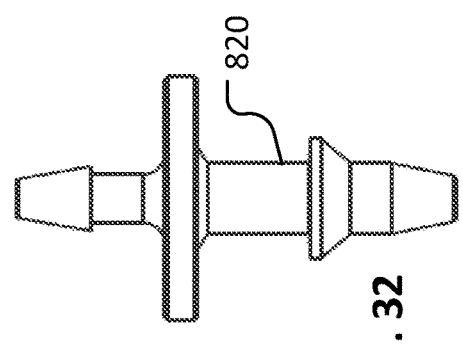
FIG. 32 is a first side view of the insert component of FIG. 29.
Figure 33:
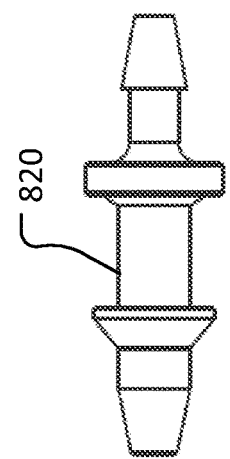
FIG. 33 is a second side view of the insert component of FIG. 29.
Figure 30:
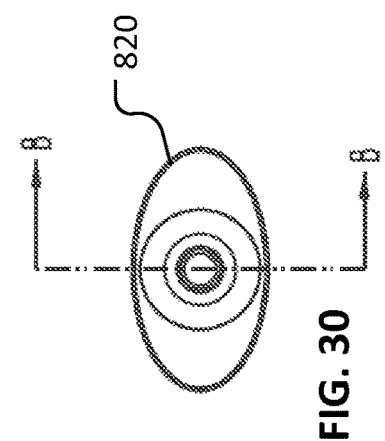
FIG. 30 is an end view of the insert component of FIG. 29.
Figure 31:
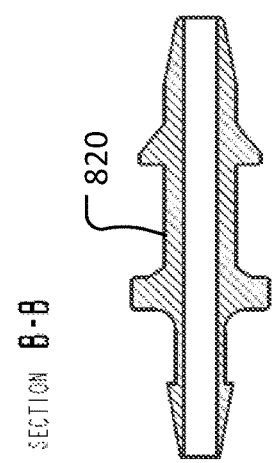
FIG. 31 is a longitudinal cross-sectional view of the insert component of FIG. 29 taken along the break line B-B of FIG. 30.
Figure 34:
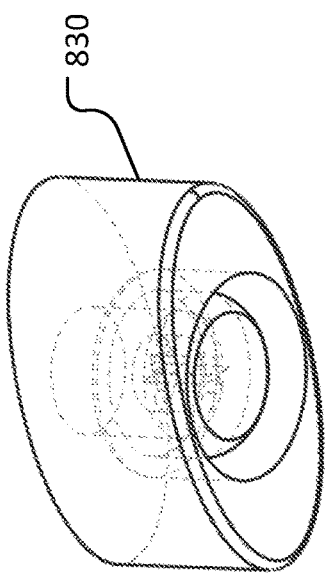
FIG. 34 is a perspective view of a seal component of the aseptic coupling of FIG. 23.
Figure 35:
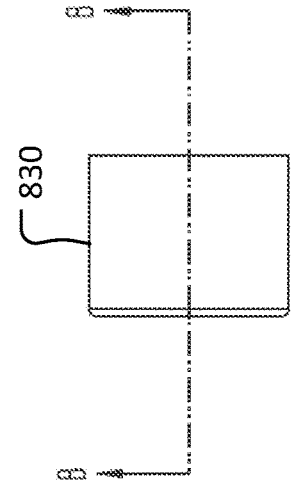
FIG. 35 is an end view of the seal component of FIG. 34.
Figure 36:
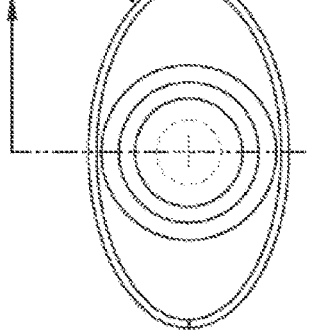
FIG. 36 is a side view of the seal component of FIG. 34.
Figure 37:
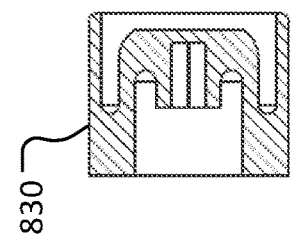
FIG. 37 is a first longitudinal cross-sectional view of the insert component of FIG. 34 taken along the break line A-A of FIG. 35.
Figure 38:
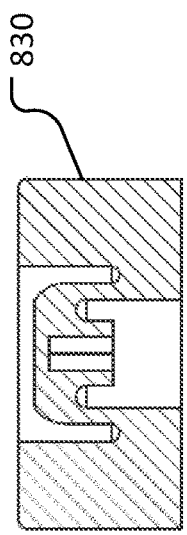
FIG. 38 is a second longitudinal cross-sectional view of the insert component of FIG. 34 taken along the break line B-B of FIG. 36.
Figure 39:
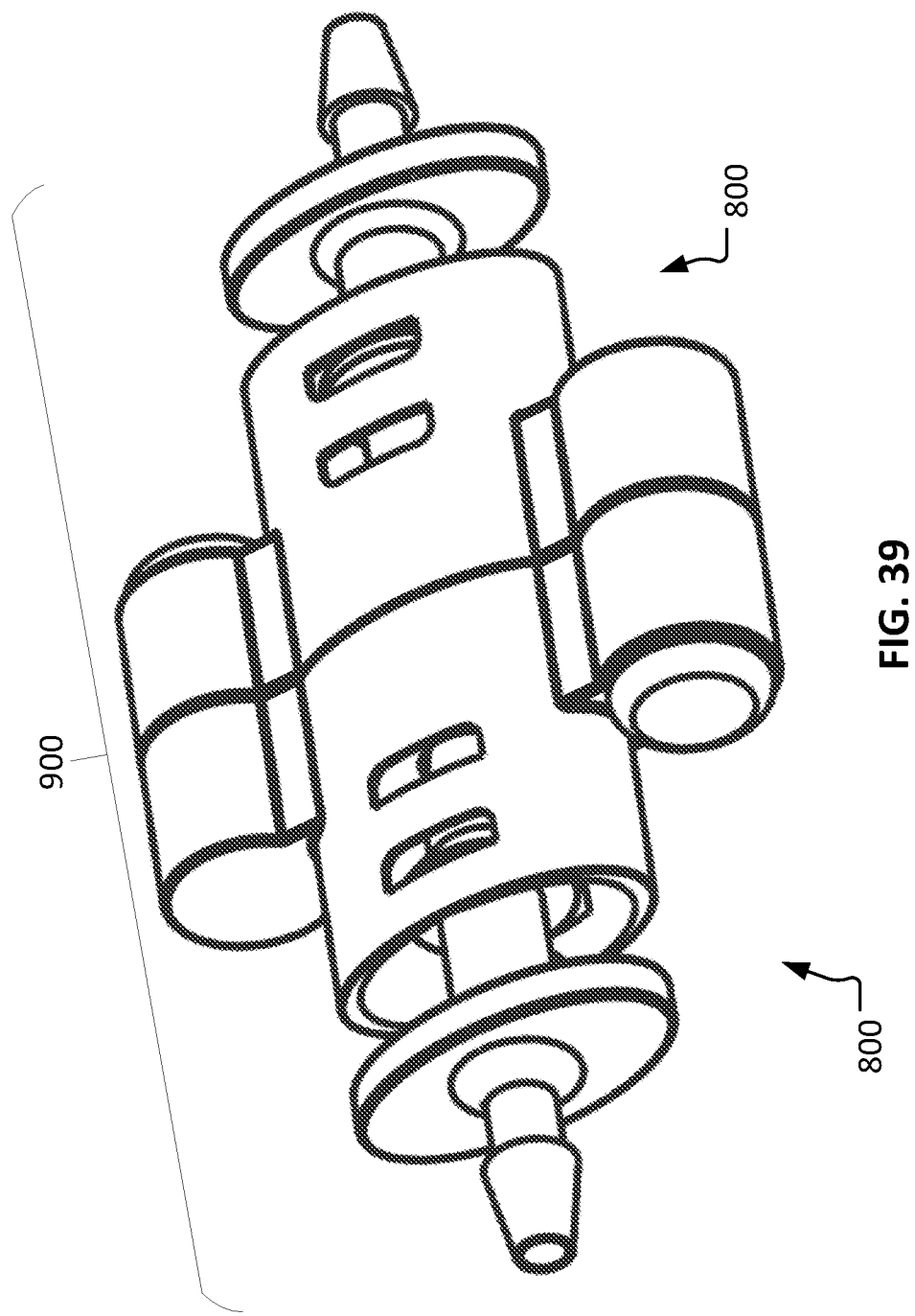
FIG. 39 is a perspective view of two of the aseptic couplings of FIG. 23 in a pre-coupled configuration.
Figure 45:
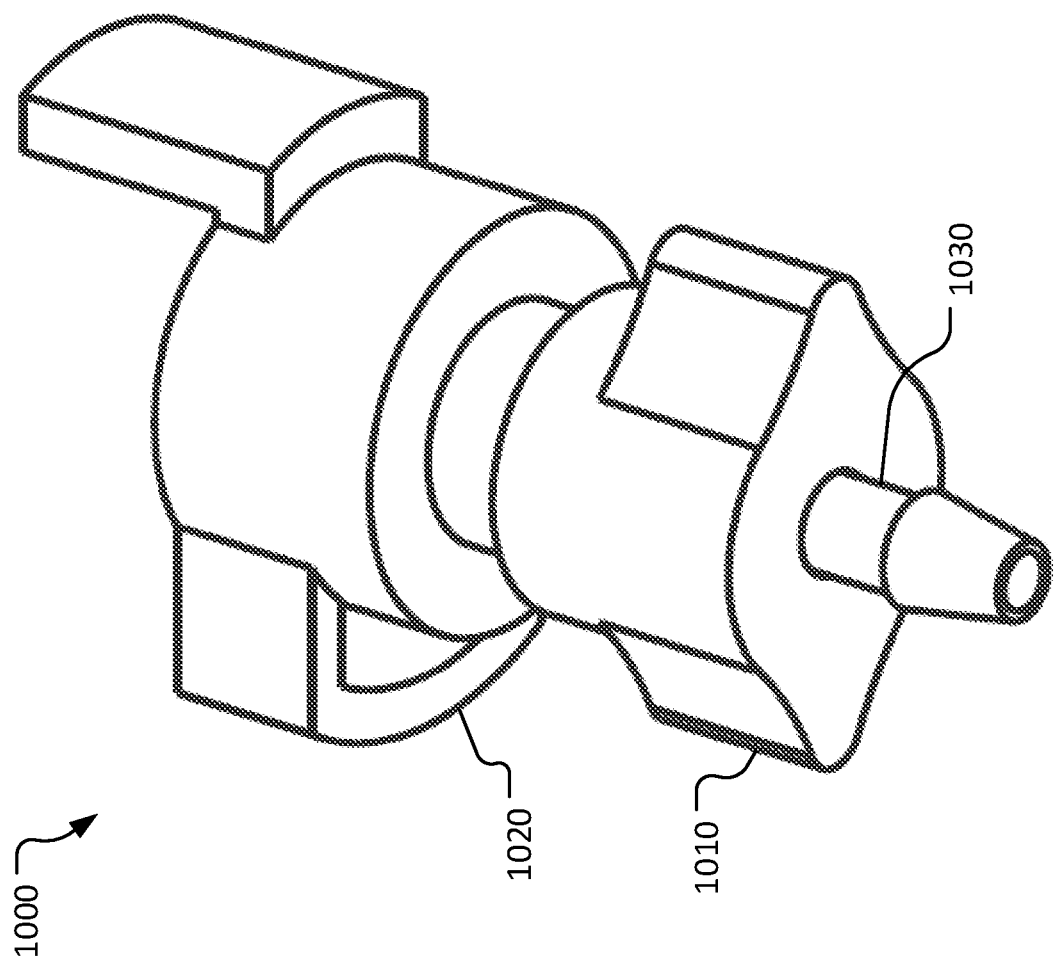
FIG. 45 is a perspective view of another example aseptic coupling in accordance with some embodiments.
Figure 47:
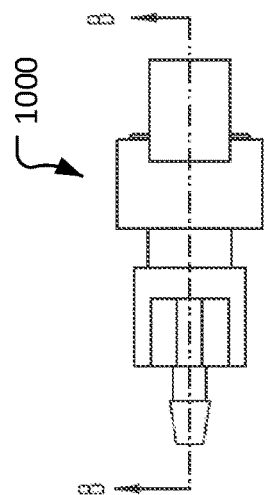
FIG. 47 is a first side view of the aseptic coupling of FIG. 45.
Figure 50:
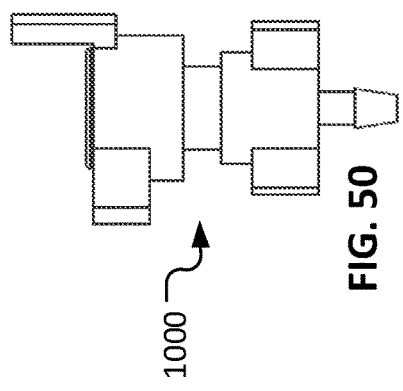
FIG. 50 is a second side view of the aseptic coupling of FIG. 45.
Figure 46:
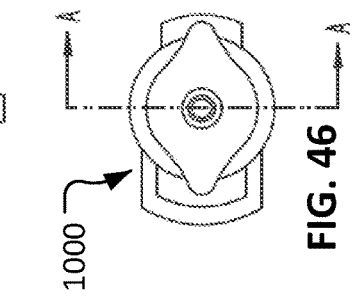
FIG. 46 is an end view of the aseptic coupling of FIG. 45.
Figure 49:
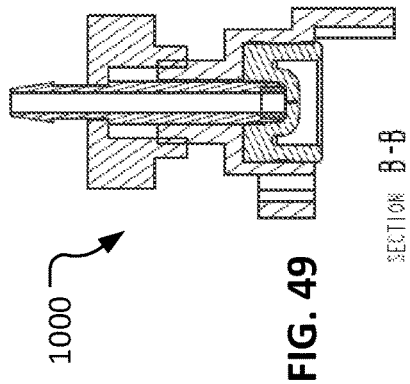
FIG. 49 is a second longitudinal cross-sectional view of the aseptic coupling of FIG. 45 taken along break line B-B of FIG. 47.
Figure 48:
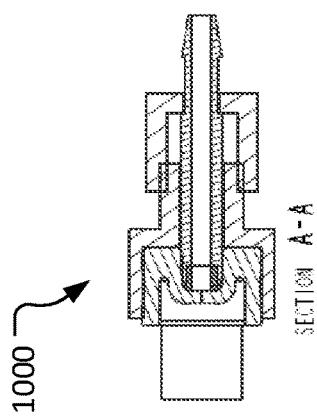
FIG. 48 is a first longitudinal cross-sectional view of the aseptic coupling of FIG. 45 taken along break line A-A of FIG. 46.
Figure 53:
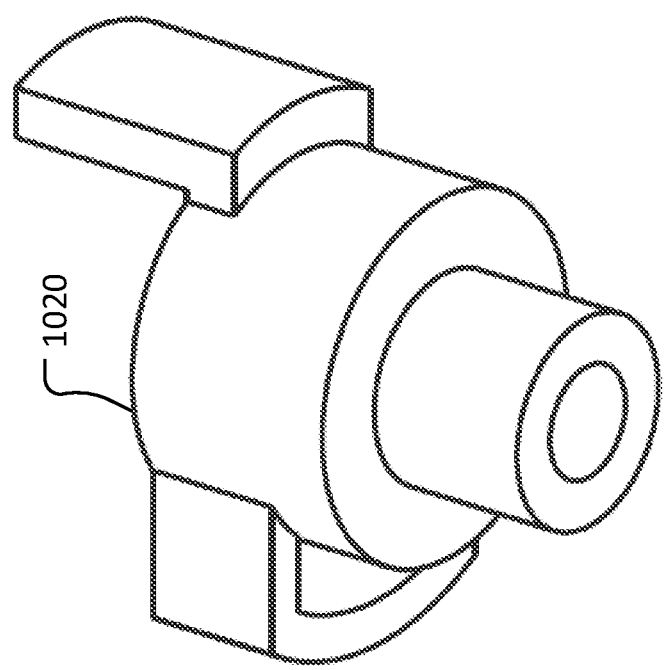
FIG. 53 is a perspective view of a seal body component of the aseptic coupling of FIG. 45.
Figure 52:
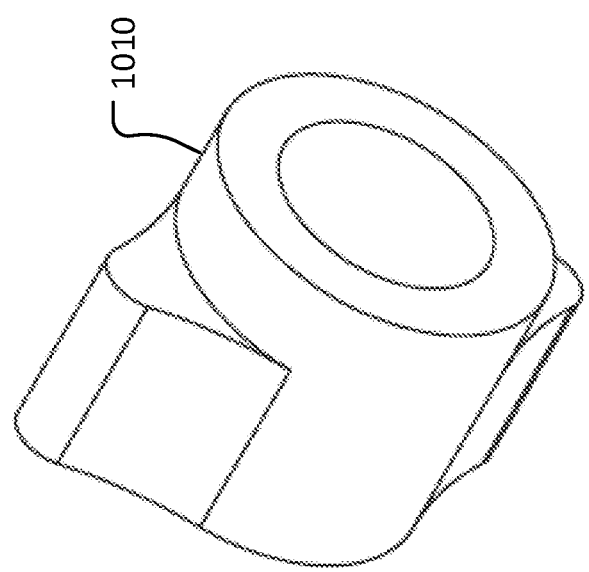
FIG. 52 is a perspective view of a twist collar component of the aseptic coupling of FIG. 45.
Figure 55:
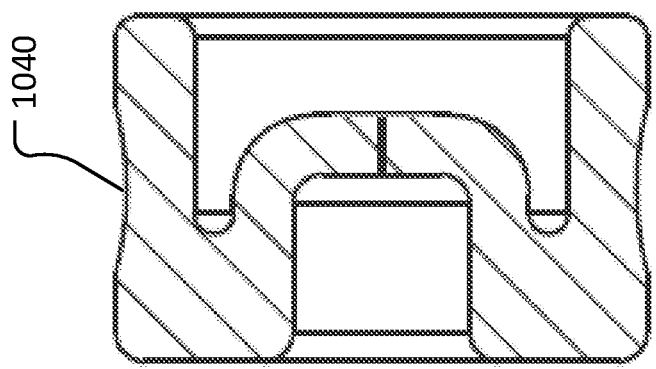
FIG. 55 is a longitudinal cross-sectional view of the seal component of FIG. 54.
Figure 54:
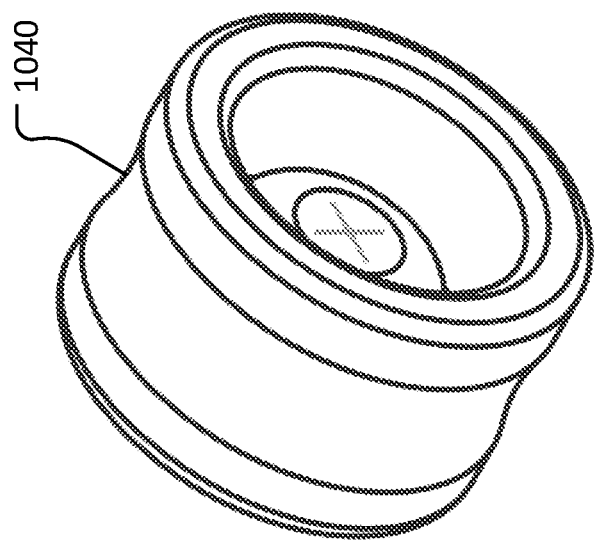
FIG. 54 is a perspective view of a seal component of the aseptic coupling of FIG. 45.
Figure 56:
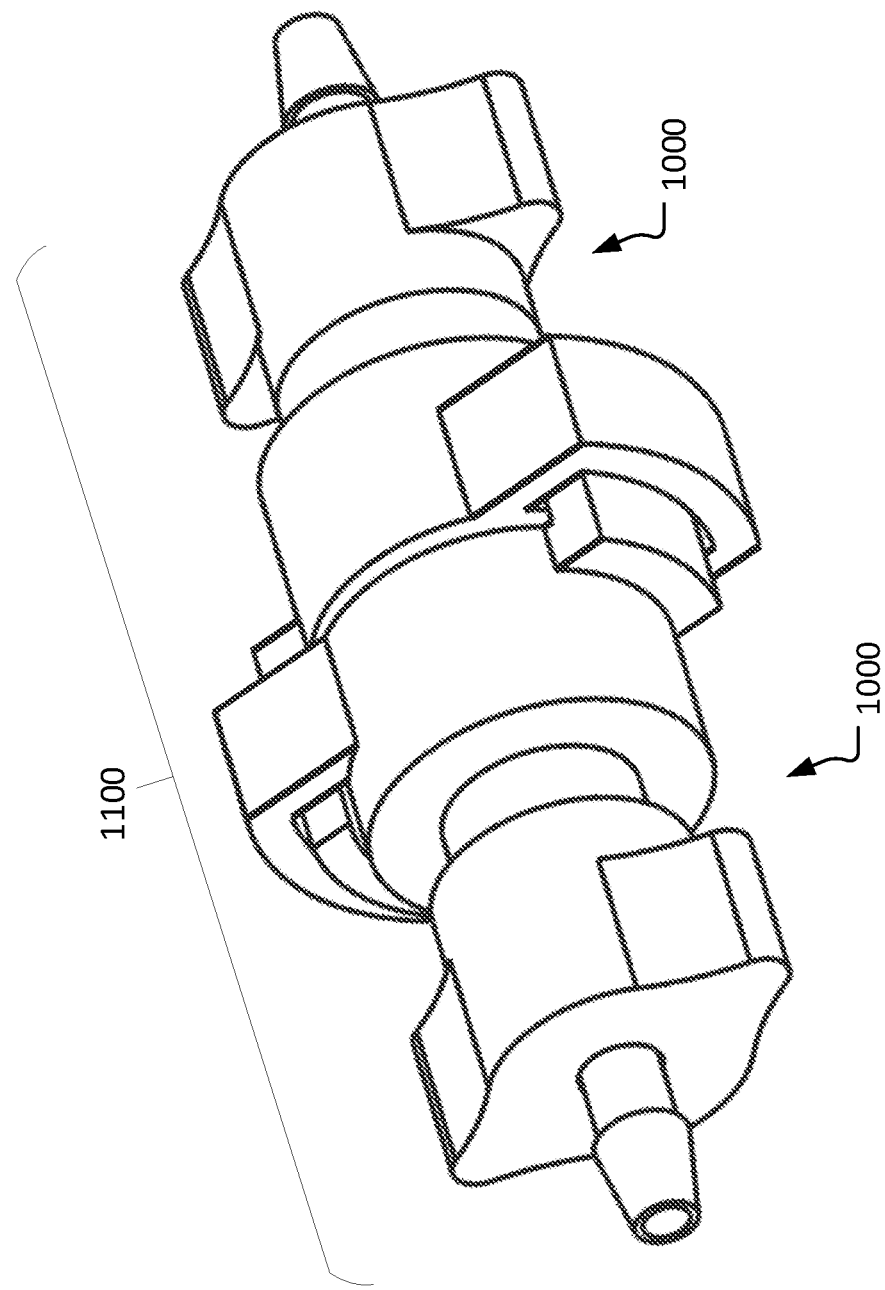
FIG. 56 is a perspective view of two of the aseptic couplings of FIG. 45 in a pre-coupled configuration.
Figure 59:
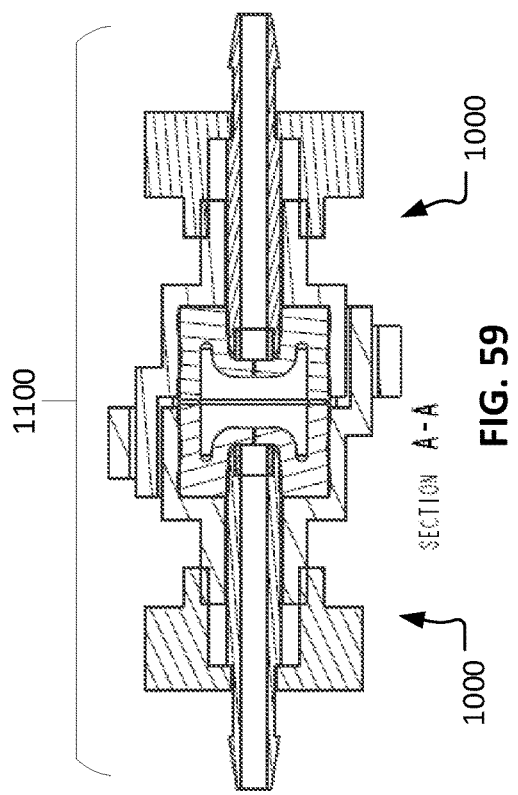
FIG. 59 is a longitudinal cross-sectional view of two of the aseptic couplings of FIG. 45 in a pre-coupled configuration.
Figure 60:
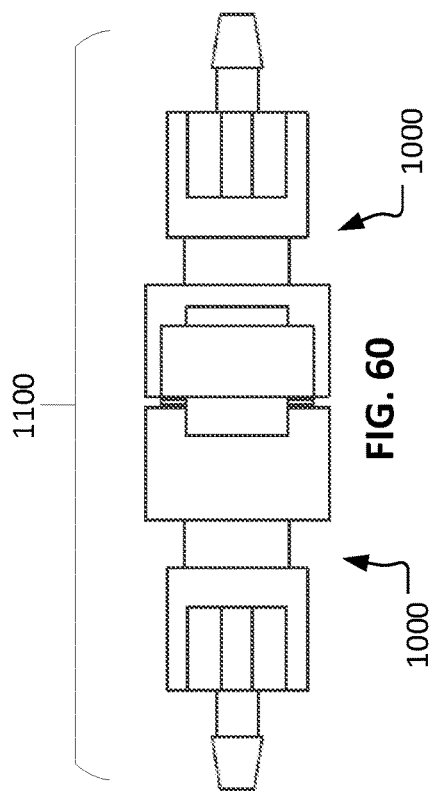
FIG. 60 is a second side view of two of the aseptic couplings of FIG. 45 in a pre-coupled configuration.
Figure 57:
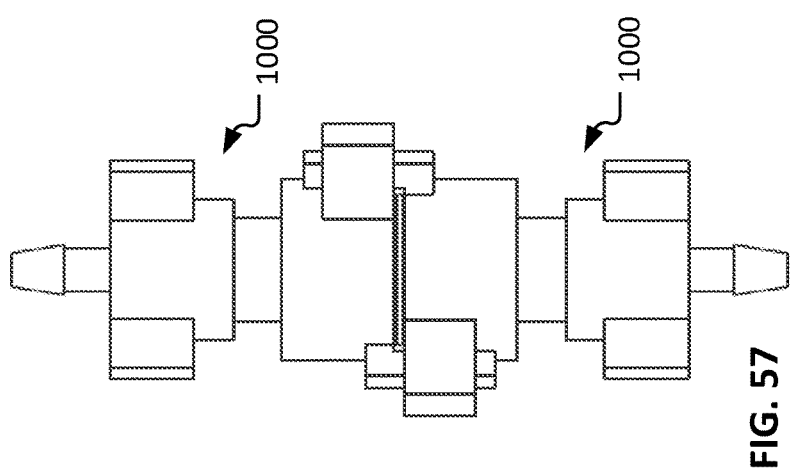
FIG. 57 is a first side view of two of the aseptic couplings of FIG. 45 in a pre-coupled configuration.
Figure 58:
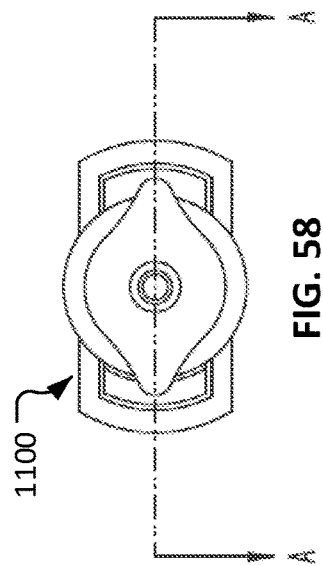
FIG. 58 is an end view of two of the aseptic couplings of FIG. 45 in a pre-coupled configuration.

FIGS. 2-7 depict a first example aseptic coupling 200. As shown in FIG. 7, two aseptic couplings 200 can be mated together to create an aseptic coupling arrangement 300 with a sterile flow path therethrough.

The aseptic coupling 200 includes a coupling portion 210 and a cover 240. The coupling portion 210 and the cover 240 are slidably coupled together (by a tongue in groove arrangement in the depicted embodiment). A detent mechanism can releasably latch the cover 240 to the coupling portion 210. When two aseptic couplings 200 are mated together in the pre-coupled or coupled state, the covers 240 become uncoupled from their respective coupling portions 210, as described further below.

A cover seal 216 (FIG. 4) is interposed between the cover 240 and the coupling portion 210. The cover 240 and the cover seal 216 prevents contamination of the internal flow path of the aseptic coupling 200 while the cover 240 is coupled to the coupling portion 210.

The coupling portion 210 includes a main body 212, a lock ring 220, a seal pusher 230, and a primary seal 236. The lock ring 220 is rotatably coupled to the seal pusher 230. The assembly of the lock ring 220 and seal pusher 230 is threadedly coupled to the main body 212. Accordingly, rotating the lock ring 220 in relation to the main body 212 will cause the lock ring 220 and seal pusher 230 to move longitudinally in relation to the main body 212 in accordance with the pitch of the threads between the lock ring 220 and the main body 212. The seal pusher 230 is in contact with the primary seal 236.

While the aseptic coupling 200 is in the uncoupled configuration (as shown in FIGS. 2-6) the primary seal 236 is set back from the front face of the main body 212 that faces toward the cover 240. Rotation of the lock ring 220 will translate the seal pusher 230 so that the primary seal 236 can be pushed toward and past the front face of the main body 212.

Figure 5:
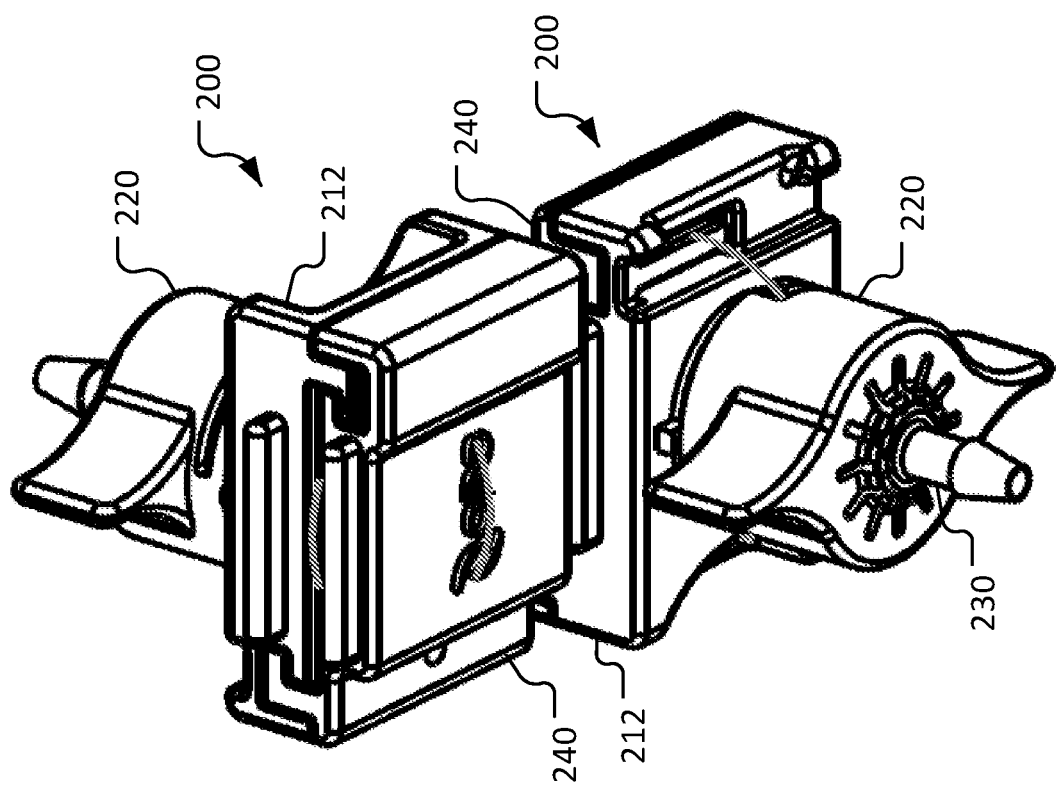
FIG. 5 is a perspective view of two of the aseptic couplings of FIG. 2 in an uncoupled configuration.

Referring specifically to FIGS. 5 and 6, two aseptic couplings 200 can be physically aligned with each other by a user in preparation for sliding them into the pre-coupled configuration. The main body 212 and cover 240 can include alignment ribs and corresponding alignment recesses to aid the user to properly align the two aseptic couplings 200. When the alignment ribs are positioned in the corresponding alignment recesses, the user can slide the coupling portions 210 (transversely to their longitudinal axes) into engagement with each other. In the process, the covers 240 will be forced to slide away from being engaged with the coupling portions 210 and will fall away.

After the coupling portions 210 are slid together, the coupling portions 210 of the two aseptic couplings 200 will become mated together as shown in FIG. 7. A detent mechanism can releasably latch the two main bodies 212 together. The sliding together of the coupling portions 210 puts the aseptic couplings 200 in the pre-coupled configuration. In that configuration, the primary seals 236 are not in contact with each other.

With the two aseptic couplings 200 in the pre-coupled configuration as shown in FIG. 7, then the lock rings 220 of each coupling portion 210 can be rotated so that the primary seals 236 are forced to move toward each other and become compressed against each other. At this point, the two aseptic couplings 200 are in the coupled configuration. A detent mechanism can latch the lock rings 220 in the coupled configuration.

FIGS. 8-13 depict a second example aseptic coupling 400. As shown in FIGS. 11-13, two aseptic couplings 400 can be mated together to create an aseptic coupling arrangement 500 with a sterile flow path therethrough.

The aseptic coupling 400 includes a main body 410, a seal pusher 420, a seal 430, and a membrane 440. The seal pusher 420 is rotatably coupled to the main body 410. The seal 430 is within the interior of the main body 410 and is abutted by the seal pusher 420. The membrane 440 is removably attached to the front face of the main body 410 to fully cover the seal 430 and to seal the interior of the main body 410 from the ambient environment. In some embodiments, the membrane 440 is ultrasonic welded, heat-sealed, or adhered to the main body 420.

In the uncoupled and pre-coupled configurations, the seal 430 is fully within the main body 410. That is the front face of the seal 430 is set back from the front face of the main body 410, and from the membrane 440.

The main body 420 includes an alignment post and an alignment guide. The alignment guide defines an open space that is shaped in a corresponding manner to the alignment post so that an alignment post from a mating coupling can be slidably received therein.

Referring specifically to FIGS. 11-13, a user can conjoin two aseptic couplings 400 together by aligning their alignment posts and alignment guides and pressing them longitudinally into engagement with each other as shown. This is the pre-coupled configuration. In some embodiments, a latch mechanism can detain the two aseptic couplings 400 together.

Next, seal pusher levers 422 extending from the seal pushers 420 can be pivoted in relation to their respective main body 410. While being pivoted, the seal pusher levers 422 travel within slots 412 defined by the main body 410. The slots 412 extend at an acute angle relative to the longitudinal axis of the main body 410. Accordingly, as the seal pushers 420 are pivoted they also move along the longitudinal axis and push the seals 430 correspondingly. When fully rotated (e.g., in a range of 80 degrees to 100 degrees), the seal pusher levers 422 are received in slots defined in the alignment posts. In some embodiments, the seal pusher levers 422 latch into the slots defined in the alignment posts.

When the seal pusher levers 422 have been rotated, the seals 430 compress or sandwich the two membranes 440 that are still between the seals 430. In fact, four layers of the membranes 440 are disposed between the two seals 430 because each of the membranes 440 is folded over on itself.

While the seals 430 are compressing the four layers of the membranes 440 therebetween, the membranes 440 can be pulled transversely as indicated by arrow P in FIG. 13. Due to the folds in the membranes 440, as the membranes 440 are pulled, the membranes 440 will effectively roll off the faces of the main bodies 410, and the seals 430 will then become abutted against each other. That creates the coupled configuration of the aseptic coupling arrangement 500.

FIGS. 14-22 depict a third example aseptic coupling 600. As shown in FIGS. 20-22, two aseptic couplings 600 can be mated together to create an aseptic coupling arrangement 700 with a sterile flow path therethrough.

The aseptic coupling 600 includes a main body 610 and a seal/pull tab 620. The main body 610 includes piercing member 612 (FIG. 21). The seal/pull tab 620 includes a seal member 622 and a pull tab 624 that are attached to each other. In some embodiments, the seal/pull tab 620 is a unitary member. In some embodiments, the seal/pull tab 620 is a unitarily-molded silicone member.

Referring specifically to FIGS. 20-22, a user can conjoin two aseptic couplings 600 together by aligning their alignment posts and alignment guides and pressing them longitudinally into engagement with each other as shown. This is the pre-coupled configuration. In some embodiments, a latch mechanism can detain the two aseptic couplings 600 together.

Additional compression of the two aseptic couplings 600 toward each other will cause the piercing members 612 to pierce and/or shear the seal/pull tabs 620. Thereafter, the pull tabs 624 can be pulled in the direction P and the pull tabs 624 will be removed from the aseptic coupling arrangement 700 while the seal members 622 remain, abutting against each other.

FIGS. 23-44 depict a fourth example aseptic coupling 800. As shown in FIGS. 39-44, two aseptic couplings 800 can be mated together to create an aseptic coupling arrangement 900 with a sterile flow path therethrough.

The aseptic coupling 800 includes a main body 810, an insert 820, and a seal 830. The seal 830 is fixedly coupled within the main body 810. The insert 820 is movably coupled in relation to the main body 810 and to the seal 830.

The main body 810 has an ovular cross-sectional shape. When a user compresses the main body 810 along the major axis of the ovular cross-sectional shape, the insert 820 is translatable along the longitudinal axis of the main body 810. In some embodiments, just pushing the insert 820 into the main body 810 will cause the main body 810 to deflect to allow the insert 820 to move farther into the main body 810. The insert 820 has two detent positions in relation to the main body 810: (i) a first position as depicted and (ii) a second position that creates the coupled configuration of two aseptic couplings 800.

As the insert 820 is moved farther into the main body 810, a leading end of the insert 820 will contact the seal 830, and pierce through the seal 830. The seal 830 can be perforated to allow the piercing to occur more readily than without perforations.

Referring specifically to FIGS. 39-44, a user can conjoin two aseptic couplings 800 together by aligning their alignment posts and alignment guides and pressing them longitudinally into engagement with each other as shown. This is the pre-coupled configuration. In some embodiments, a latch mechanism can detain the two aseptic couplings 800 together.

While the two aseptic couplings 800 are coupled together, a user can advance the inserts 820 into the main bodies 810 (to their second positions). In doing so, the seals 830 will be pierced. When the seals 830 become pierced, portions of the opposing seals 830 will become displaced into contact with each other to create a fluid seal therebetween. The tips of the inserts 820 will be spaced apart from each other, and the seals 830 will contact each other to establish a sealed sterile flow path through the aseptic coupling arrangement 900. This is the coupled configuration.

FIGS. 45-60 depict a fifth example aseptic coupling 1000. As shown in FIGS. 56-60, two aseptic couplings 1000 can be mated together to create an aseptic coupling arrangement 1100 with a sterile flow path therethrough.

The aseptic coupling 1000 includes a twist collar 1010, a seal body 1020, a plunger 1030, and a seal 1040. The seal 1040 is fixedly coupled within the seal body 1020. The twist collar 1010 is threadedly coupled to the seal body 1020. As the twist collar 1010 is rotated in relation to the seal body 1020, the twist collar 1010 drives the plunger 1030 toward the seal 1040.

Referring specifically to FIGS. 56-60, a user can conjoin two aseptic couplings 1000 together by aligning their alignment posts and alignment guides and pressing them longitudinally into engagement with each other as shown. This is the pre-coupled configuration. In some embodiments, a latch mechanism can detain the two aseptic couplings 1000 together.

A user can then rotate the twist collars 1010 relative to their respective seal bodies 1020. The rotation will drive the plungers 1030 toward the seals 1040 and the tips of the plungers 1030 will pierce through the seals 1040. In some embodiments, the seal 1040 includes perforations (e.g., in a plus sign "+" pattern, FIG. 54) to facilitate the piercing of the plungers 1030. The plungers 1030 include a tip seal 1032 (FIG. 51). As the plungers 1030 pierce through the seals 1040, the tip seals 1032 can abut against each other to create an aseptic coupling arrangement 1100 with a sterile flow path therethrough.

FIGS. 61-68 depict another example aseptic coupling 1200. As shown in FIGS. 69-72, two aseptic couplings 1200 can be mated together to create an aseptic coupling arrangement 1300 with a sterile flow path therethrough.

Figure 63:
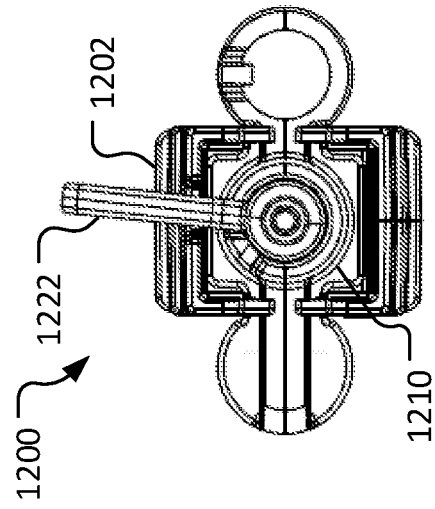
FIG. 63 is an end view of the aseptic coupling of FIG. 61.
Figure 62:
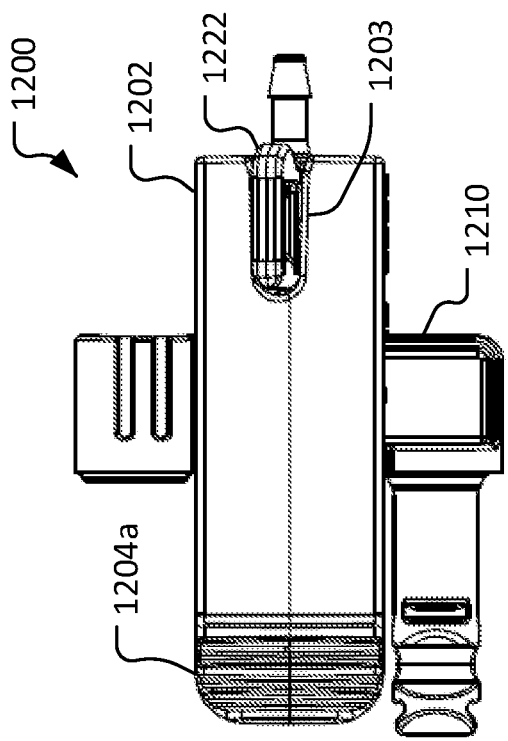
FIG. 62 is a top view of the aseptic coupling of FIG. 61.
Figure 61:
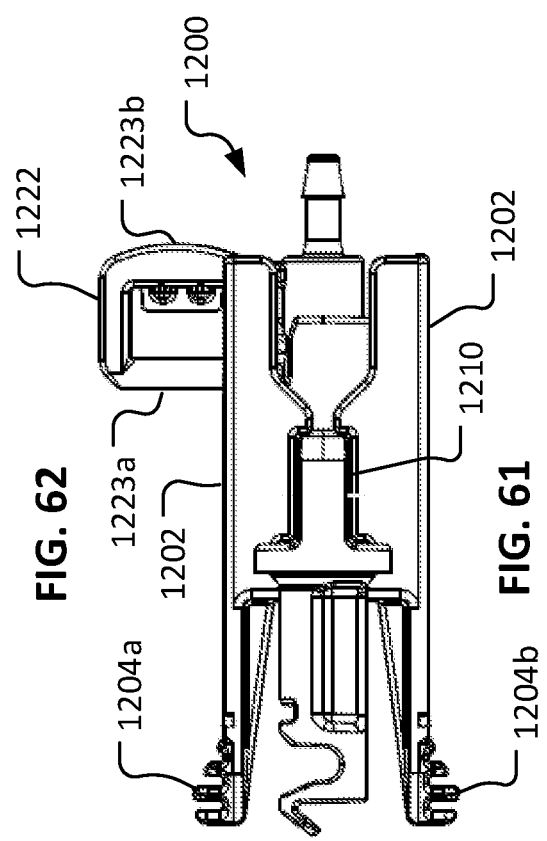
FIG. 61 is a side view of another example aseptic coupling in accordance with some embodiments.
Figure 68:
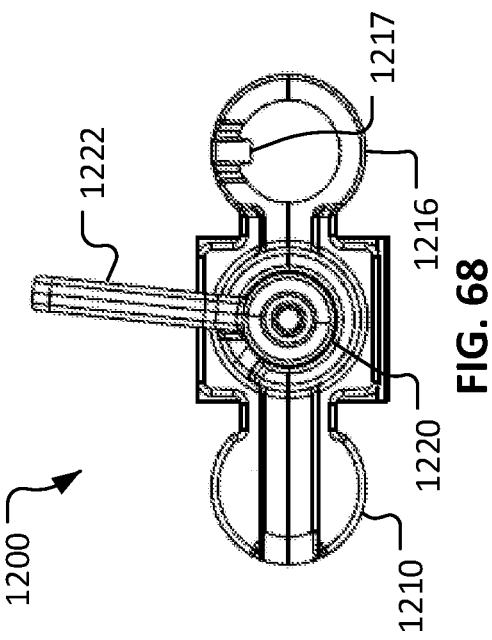
FIG. 68 is an end view of the aseptic coupling of FIG. 61 with the protective cover removed.

As shown in FIGS. 61-63, a protective cover 1202 can be releasably attached to a main body 1210 of the coupling 1200. The protective cover 1202 can serve to protect the membrane 1240 (not visible) during shipping and handling. The protective cover 1202 also maintains the rotational position of a seal pusher lever 1222 that extends through an open-ended slot 1203 defined by the protective cover 1202. In addition, the presence of the protective cover 1202 can help facilitate manual handling of the coupling 1200.

In the depicted embodiment, the protective cover 1202 includes a first grip portion 1204*a* and a second grip portion 1204*b* that are on opposite sides of the protective cover 1202. To remove the protective cover 1202 from the coupling 1200, the user can manually pinch the grip portions 1204*a-b* toward each other to open the opposite end of the protective cover 1202, and then longitudinally pull the protective cover 1202 away from the coupling 1200.

With the protective cover 1202 removed, the coupling 1200 is entirely visible, such as depicted in FIGS. 64-68.

The aseptic coupling 1200 includes the main body 1210, a seal pusher 1220 with its seal pusher lever 1222 extending radially, a seal 1230, and a membrane 1240. The seal pusher 1220 is rotatably coupled to the main body 1210. The seal pusher lever 1222 includes a first radially-extending member 1223*a* and a second radially-extending member 1223*b*.

The seal 1230 is within the interior of the main body 1210 and is abutted by the seal pusher 1220. The membrane 1240 is removably attached to the front face of the main body 1210 to cover fully the seal 1230 and to seal the interior of the main body 1210 from the ambient environment. In some embodiments, the membrane 1240 is ultrasonic welded, heat-sealed, or adhered to the main body 1220.

In some embodiments, while the aseptic coupling 1200 is in the uncoupled and pre-coupled configurations, the seal 1230 is fully within the main body 1210. That is the front face of the seal 1230 is set back from the front face of the main body 1210, and from the membrane 1240. Alternatively, in some embodiments the seal 1230 protrudes slightly from the front face of the main body 1210 while the aseptic coupling 1200 is in the uncoupled and pre-coupled configurations.

Figure 66:
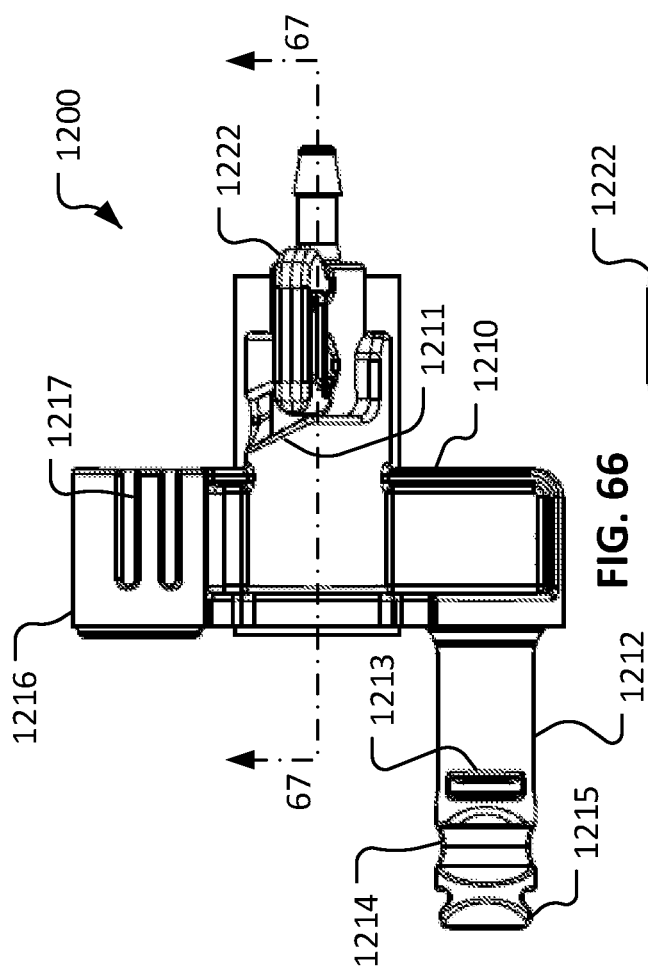
FIG. 66 is a top view of the aseptic coupling of FIG. 61 with the protective cover removed.
Figure 67:
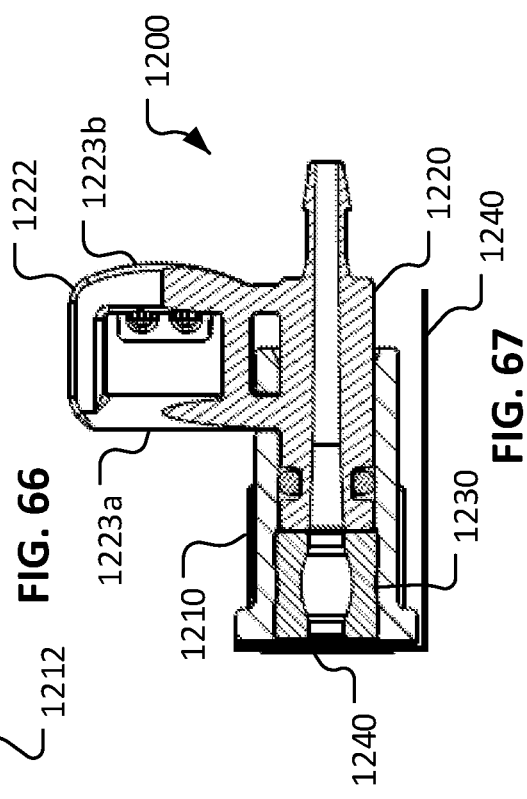
FIG. 67 is a longitudinal cross-sectional view of the aseptic coupling of FIG. 61 taken along break line 67-67 of FIG. 66.
Figure 74:
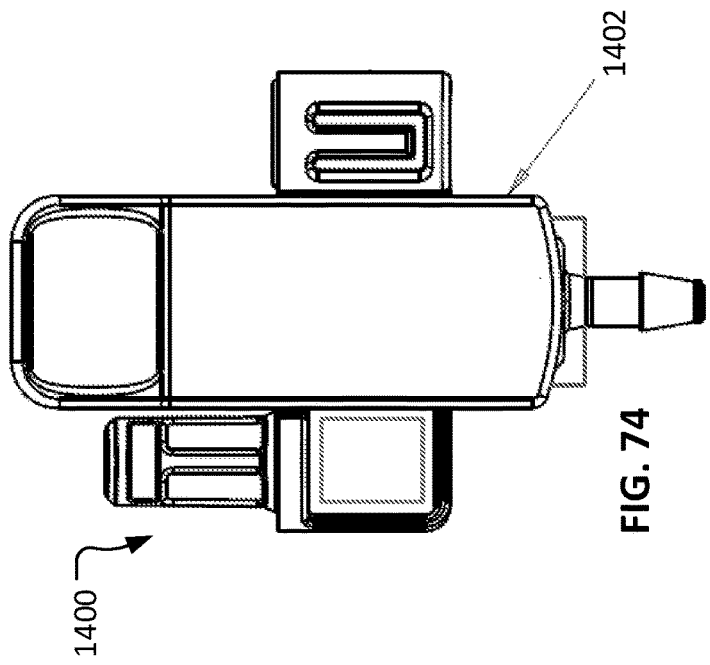
FIG. 74 is a top view of the aseptic coupling of FIG. 73.
Figure 75:
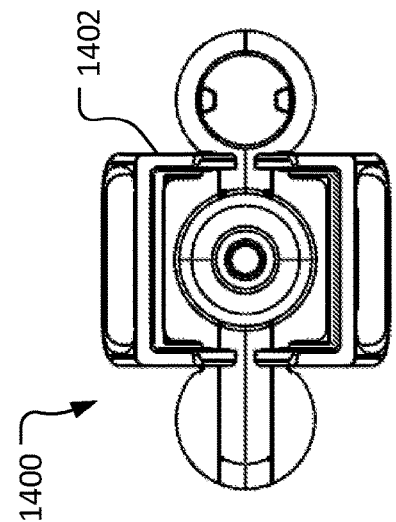
FIG. 75 is an end view of the aseptic coupling of FIG. 73.
Figure 73:
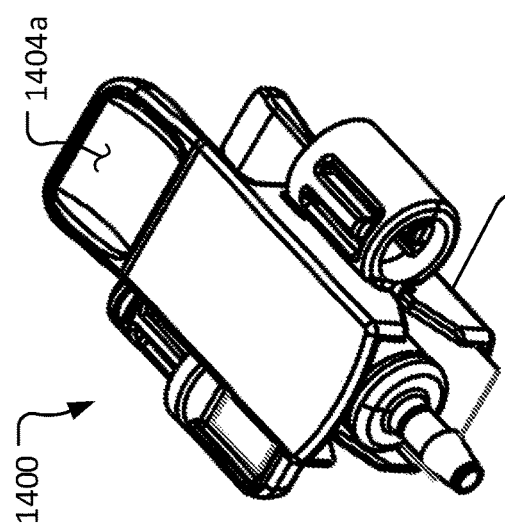
FIG. 73 is a perspective view of another example aseptic coupling in accordance with some embodiments.

The main body 1210 includes an alignment post 1212 and an alignment guide 1216. The alignment guide 1216 defines an open space that is shaped in a corresponding manner to the alignment post 1212 so that an alignment post 1212 from a mating coupling 1200 can be slidably received therein. The alignment post 1212 defines a notch 1213 and a transverse groove 1214. The free end of the alignment post 1212 includes a latch member 1215. The alignment guide 1216 includes a latch member 1217 that, as shown in FIG. 66, radially extends into the open space defined by the alignment guide 1216.

Referring specifically to FIGS. 69-72, a user can conjoin two aseptic couplings 1200 together by aligning the alignment post 1212 of a first one of the couplings 1200 with the alignment guide 1216 of a second one of the couplings 1200 (and by aligning the alignment guide 1216 of the first one of the couplings 1210 with the alignment post 1212 of the second one of the couplings 1200) and then pressing them longitudinally into engagement with each other as shown to form the aseptic coupling arrangement 1300. When the two aseptic couplings 1200 are fully pressed against each other, the latch members 1217 engage into the notches 1213 to detain the two aseptic couplings 400 together longitudinally. This is a first pre-coupled configuration.

Next, seal pusher levers 1222 extending from the seal pushers 1220 can be pivoted in relation to their respective main body 1210. While being pivoted, the seal pusher levers 1222 travel within slots 1211 defined by the main body 1210. The slots 1211 extend at an acute angle relative to the longitudinal axis of the main body 1210. Accordingly, as the seal pushers 1220 are pivoted they also move along the longitudinal axis and push the seals 1230 toward the mated coupling 1200 correspondingly. When fully rotated (e.g., in a range of 80 degrees to 100 degrees), the seal pusher levers 1222 are received by the alignment posts 1212. In particular, the first radially-extending members 1223*a* are received in the transverse grooves 1214 and the second radially-extending members 1223*b* are engaged by the latch members 1215 to latch the seal pushers 1220 in the orientation in which the seals 1230 are pushed toward each other (with the membranes 1240 therebetween). This is a second pre-coupled configuration.

When the seal pusher levers 1222 have been rotated, the seals 1230 compress or sandwich the two membranes 1240 that are still between the seals 1230. In fact, four layers of the membranes 1240 are disposed between the two seals 1230 because each of the membranes 1240 is folded over on itself.

While the seals 1230 are compressing the four layers of the membranes 1240 therebetween, the membranes 1240 can be pulled transversely away from the couplings 1200. Due to the folds in the membranes 1240, as the membranes 1240 are pulled, the membranes 1240 will effectively roll off the faces of the main bodies 1210, and the seals 1230 will then become abutted against each other. That creates the coupled configuration of the aseptic coupling arrangement 1300.

FIGS. 73-89 depict another example aseptic coupling 1400. The aseptic coupling 1400 is a genderless coupling. That is, as shown in FIGS. 86-89, two aseptic couplings 1400 can be mated together to create an aseptic coupling arrangement 1500 with a sterile flow path therethrough (flow path 1501 along the longitudinal axis of the aseptic couplings 1400, FIG. 89).

Figure 76:
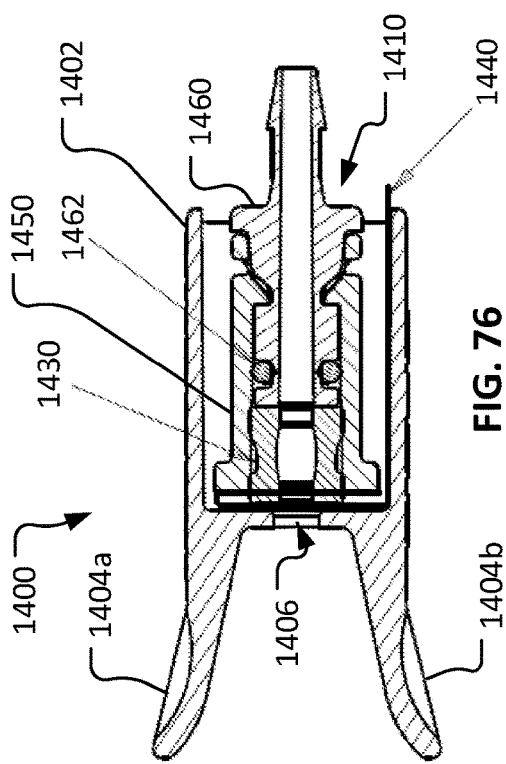
FIG. 76 is a longitudinal cross-sectional view of the aseptic coupling of FIG. 73.

As shown in FIGS. 73-76, a protective cover 1402 can be releasably attached to a main body 1410 of the coupling 1400. The protective cover 1402 can serve to protect the membrane 1440 during shipping and handling. The protective cover 1402 also abuts against the membrane 1440 (i.e., the two layers of the membrane 1440 as shown in FIG. 76) where the membrane 1440 is adjacent the front face of the main body 1410. Accordingly, the protective cover 1402 helps to support or reinforce the attachment of the membrane 1440 to the front face of the main body 1410 around the seal 1430. This reinforcement may be beneficial because, for example, during sterilization the coupling 1440 may be exposed to heat and/or pressure changes that may tend to stress the adherence between the membrane 1440 and the main body 1410. The protective cover 1402 defines an opening 1406 that is aligned with the longitudinal axis and fluid flow path of the main body 1410. In addition, the presence of the protective cover 1402 can help facilitate manual handling of the coupling 1400.

In the depicted embodiment, the protective cover 1402 includes a first grip portion 1404a and a second grip portion 1404b that are on opposite sides of the protective cover 1402. To remove the protective cover 1402 from the main body 1410, the user can manually pinch the grip portions 1404a-b toward each other to open the opposite end of the protective cover 1402, and then longitudinally pull the protective cover 1402 away from the main body 1410. With the protective cover 1402 removed, the main body 1410 and the membrane 1440 are entirely visible, such as depicted in FIGS. 77-81.

FIGS. 77-81 show various views of the main body 1410 and the membrane 1440. The membrane 1440 is releasably attached to the main body 1410. The membrane 1440 is removably attached to the front face of the main body 1410 to fully cover the seal 1430 (FIG. 76) and to seal the interior of the main body 1410 from the ambient environment. In some embodiments, the membrane 1440 is ultrasonic welded, heat-sealed, adhered, or otherwise removably attached to the main body 1420.

The membrane 1440 is a thin, flexible member. The membrane 1440 can be made of materials such as, but not limited to, polyethersulfone (PES), non-woven polyethylene such as Tyvek®, a PES and polyester laminate, expanded polytetrafluoroethylene (ePTFE), metallic foil, and the like, and combinations thereof. In some embodiments, the membrane 1440 is hydrophobic and breathable. In particular embodiments, the pore size of the membrane 1440 is such that microorganisms larger than 0.2 microns are filtered out.

The membrane 1440 includes a 180° fold 1442 and a tail end portion 1444. When, as described further below, when two aseptic couplings 1400 are mated together in a pre-coupled configuration, the membranes 1440 are then manually removed to create an open flow path through the coupled two aseptic couplings 1400 (this is referred to as the coupled configuration).

When two aseptic couplings 1400 are mated together in a pre-coupled configuration, the tail end portions 1444 of the two flexible membranes 1440 can be manually manipulated to be abutted against each other. Then, the membranes 1440 can be removed from the pre-coupled aseptic couplings 1400 by pulling on the tail end portions 1444 of the membranes 1440. That is, a user can manually grasp the tail end portions 1444 of the two membranes 1440 (e.g., grasping both tail end portions 1444 simultaneously) and simultaneously pull on the membranes 1440 transversely away from the longitudinal axes of the two aseptic couplings 1400. Pulling the membranes 1440 transversely away from the longitudinal axes of the two aseptic couplings 1400 will cause the folds 1442 to progress in the transverse direction of the pulling by rolling. As the folds 1442 roll in that manner, the membranes 1440 are being removed from the front faces of the two aseptic couplings 1400. As the membranes 1440 are removed from the front faces, the seals 1430 eventually make contact with each other and a sterile flow path through the two aseptic couplings 1400 is created.

Figure 82:
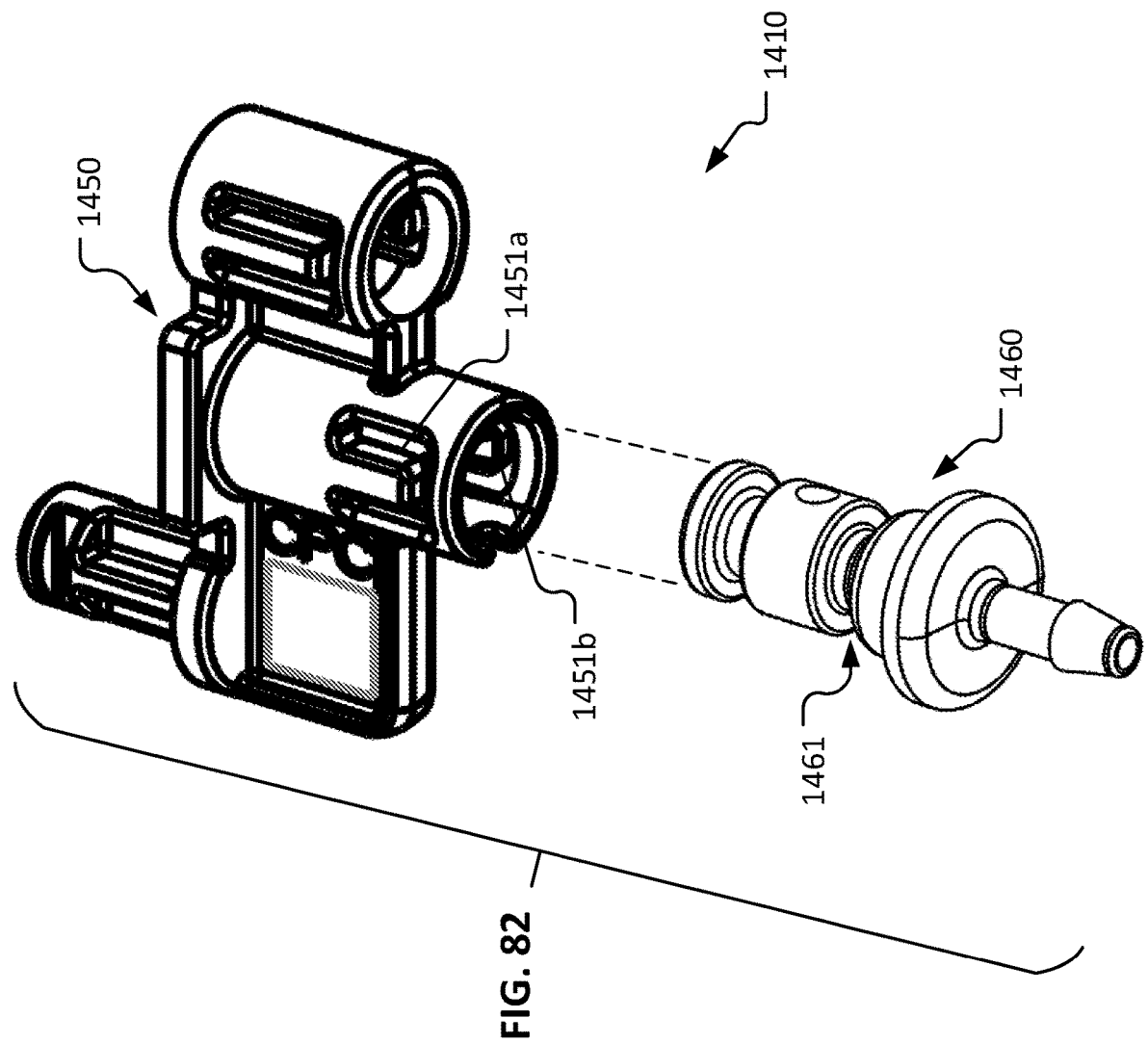
FIG. 82 is an exploded view of the main body of the aseptic coupling of FIG. 73 showing the body member and termination member separated from each other.

As shown in FIG. 82, the main body 1410 can be, optionally, a two-piece construction. That is, in the depicted embodiment the main body 1410 includes a body 1450 and a termination member 1460. A seal 1462 (FIG. 76) can be disposed between the body 1450 and the termination member 1460 to provide a fluid-tight construction.

In the depicted embodiment, the termination member 1460 conveniently snaps into engagement with the body 1450. That is, the body 1450 includes two latch members 1451a and 1451b that each engage into a circumferential groove 1461 of the termination member 1460 to detain the body 1450 and the termination member 1460 together longitudinally. This snap-in arrangement makes for efficiency when configuring the aseptic couplings 1400 with various types of termination members 1460 (e.g., a barbed connection as shown, a threaded connection, an elbow fitting, a Tee fitting, a compression fitting, etc.). In the depicted embodiment, the termination member 1460 is rotatable about its longitudinal axis in relation to the body 1450. In other words, the termination member 1460 can swivel in relation to the body 1450. In some embodiments, the termination member 1460 is configured to prevent swiveling (e.g., by using a flat or a keyway at the connection between the termination member 1460 and the body 1450).

Figure 85:
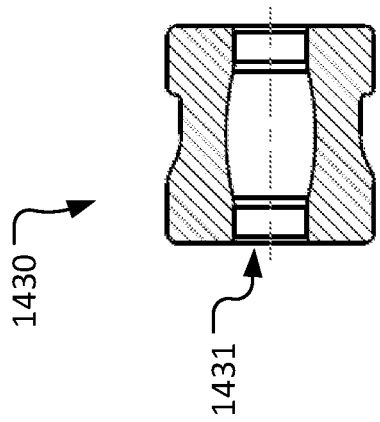
FIG. 85 is a longitudinal cross-sectional view of the seal member of FIG. 83.
Figure 84:
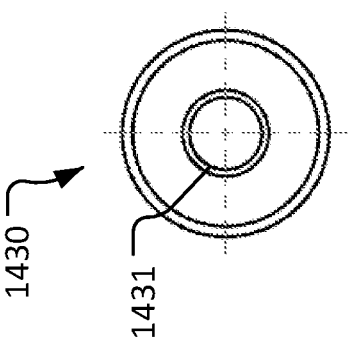
FIG. 84 is an end view of the seal member of FIG. 83.
Figure 83:
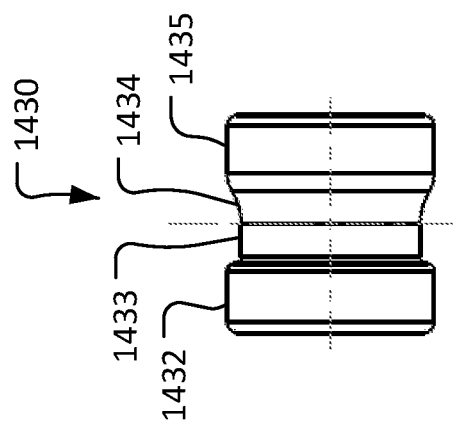
FIG. 83 is a side view of a seal member of the aseptic coupling of FIG. 73.
Figure 86:
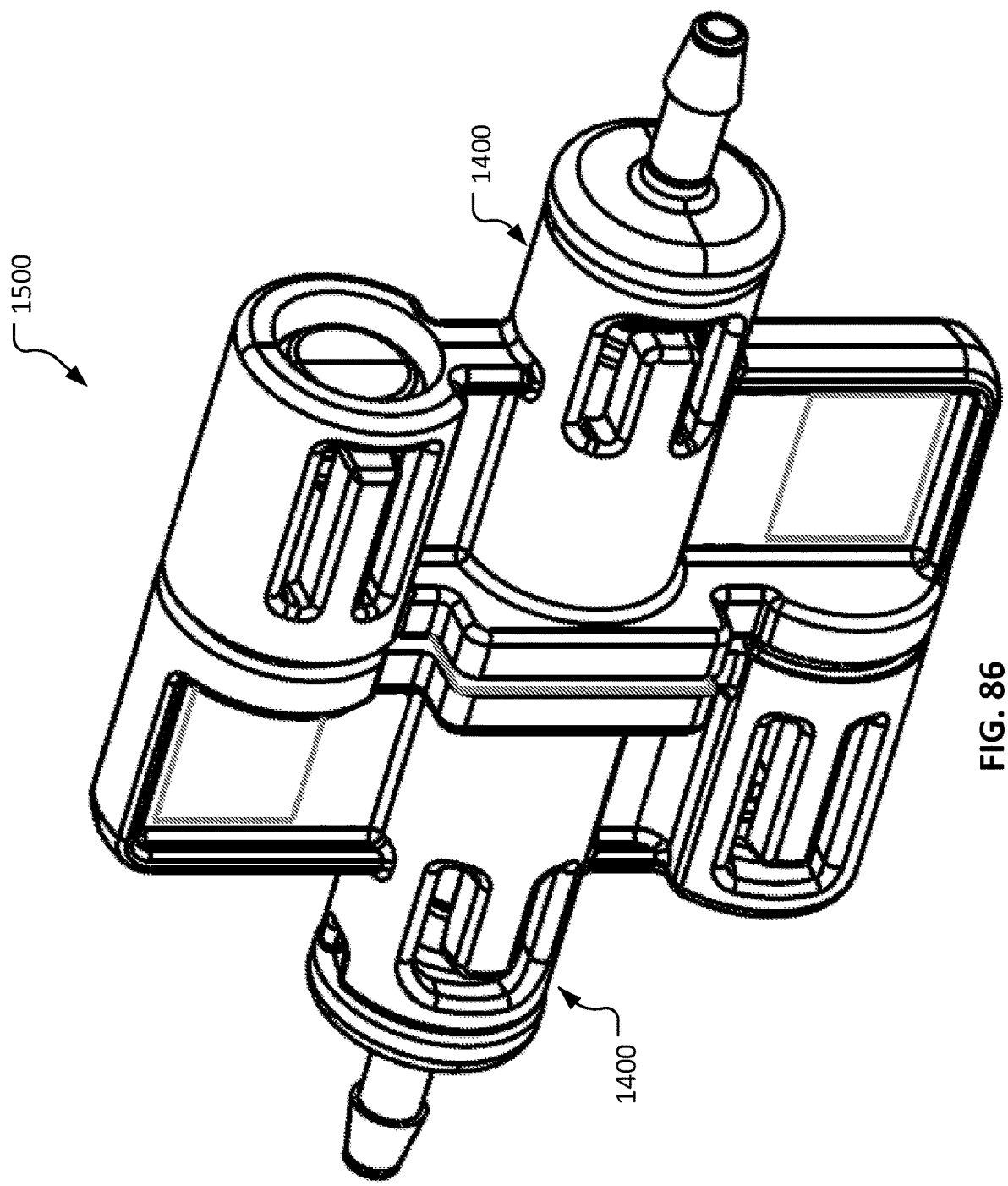
FIG. 86 is a perspective view showing two of the aseptic couplings of FIG. 73 in a coupled arrangement.

FIGS. 83-85 illustrate an example seal 1430. This seal 1430 (while shown here in isolation) is positioned in a central bore defined by the body 1450 (FIG. 76) such that an end portion of the seal 1430 protrudes slightly from the front face of the body 1450 (while being covered by the membrane 1440). In some embodiments, the other end of the seal 1430 and the end of the termination member 1460 abut each other within the bore of the body 1450 (FIG. 76).

In the depicted embodiment, the seal 1430 defines a central longitudinal bore 1431. The outer diameter of the seal 1430 includes a first cylindrical end portion 1432, a second cylindrical end portion 1435, and a waist portion between the end portions 1432 and 1435. The outer diameter of the waist portion is smaller than the outer diameters of the end portions 1432 and 1435, and comprises a cylindrical portion 1433 and a frustoconical portion 1434. The bore 1431 comprises two cylindrical end portions and a central portion (between the cylindrical end portions) that is a segment of an ovoid (with its ends truncated). In some embodiments, the waist portion of the seal's 1430 outer diameter is arcuate (rather than having the cylindrical portion 1433 and the frustoconical portion 1434). In such a case, the center of the arc of the outer diameter is located in an opposite direction in comparison to the center of the arc of the internal central portion. In some such embodiments, the arc radii of the arc of the outer diameter and the arc of the internal central portion are unequal. In some such embodiments, the arc radii of the arc of the outer diameter and the arc of the internal central portion are equal.

FIGS. 86-89 show two aseptic couplings 1400 coupled together to create an aseptic coupling arrangement 1500 with a sterile flow path 1501 therethrough. These figures depict the two aseptic couplings 1400 coupled together after the removal of the membranes 1440 (FIGS. 76-81). In some embodiments, the sequence of events for creating the aseptic coupling arrangement 1500 is: (i) removal of the protective covers 1402 from two aseptic couplings 1400, (ii) snapping together aseptic couplings 1400 so that portions of the membranes 1440 are compressed between the two seals 1430 of the aseptic couplings 1400 (this is the pre-coupled configuration), and (iii) manually pulling the membranes 1440 transversely away from the main bodies 1410 so that the two seals 1430 of the aseptic couplings 1400 become exposed and press against each other (this is the operative, coupled configuration) (e.g., see FIG. 89).

Figure 77:
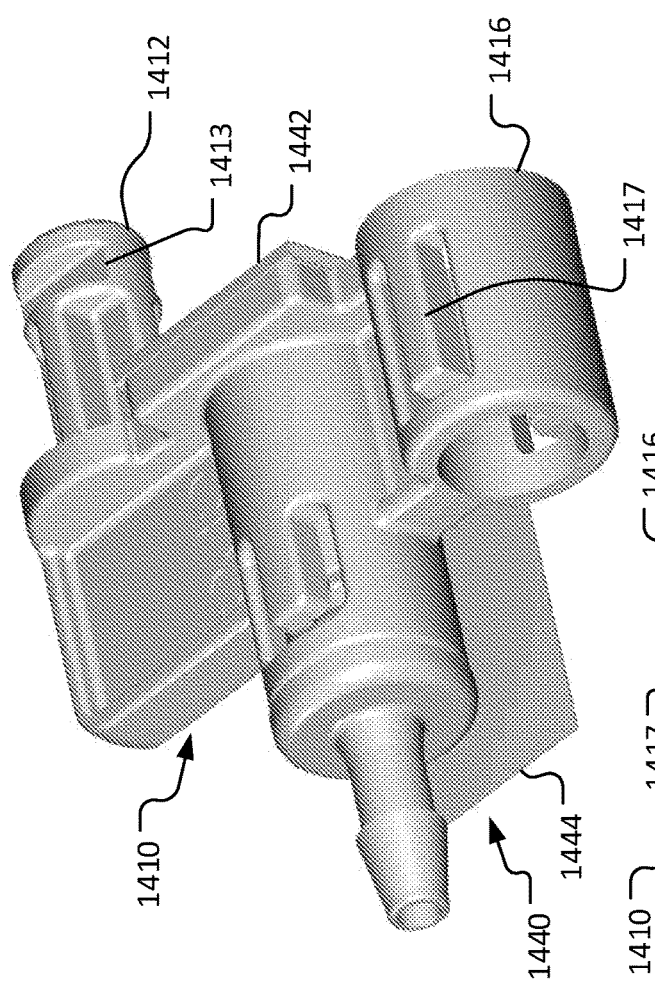
FIG. 77 is a first perspective view of the aseptic coupling of FIG. 73 without its protective cover.
Figure 78:
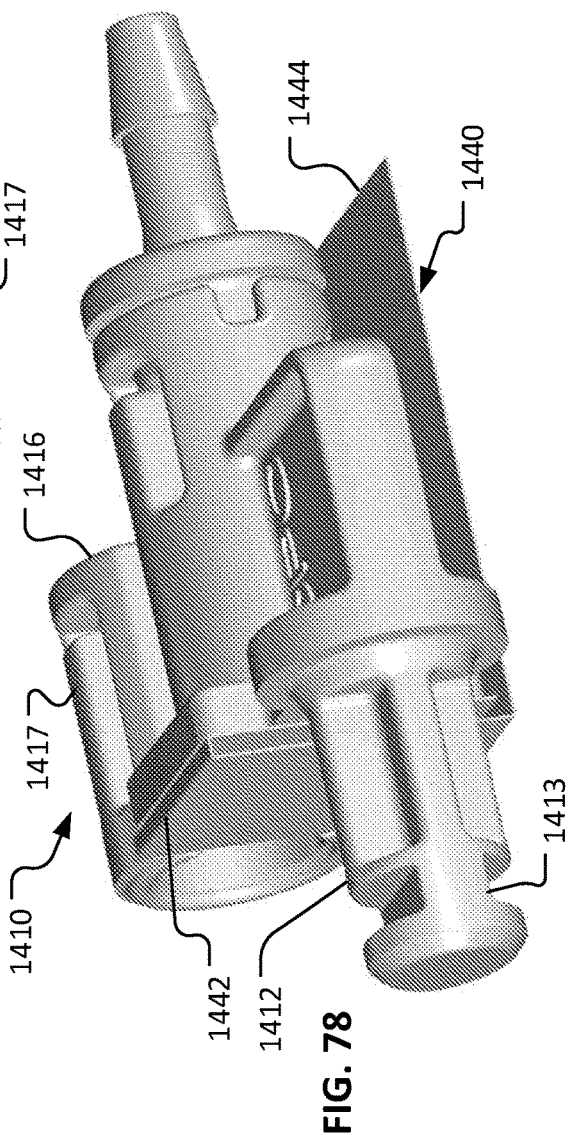
FIG. 78 is another perspective view of the aseptic coupling of FIG. 73 without its protective cover.
Figure 81:
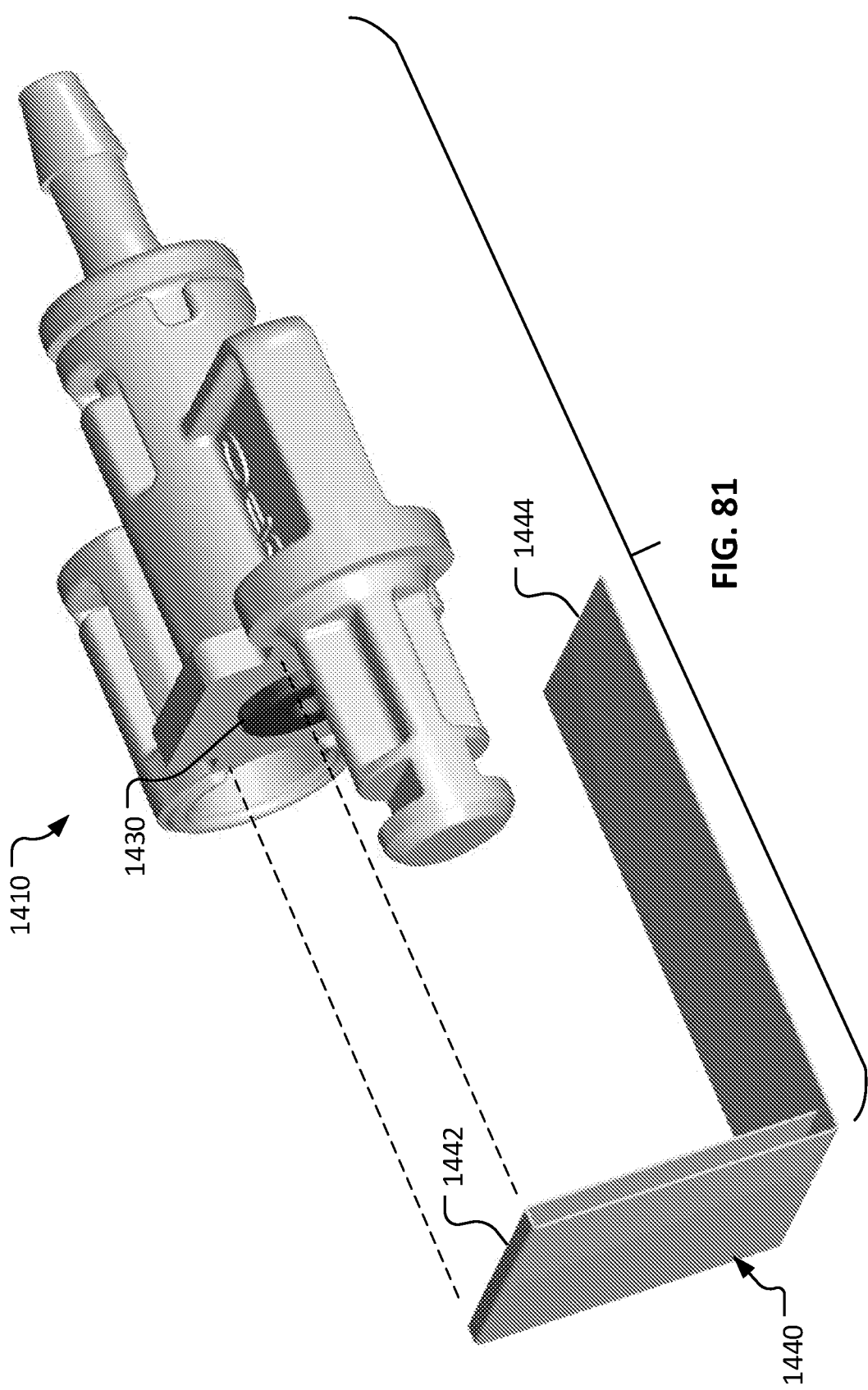
FIG. 81 is an exploded view of the main body and membrane of the aseptic coupling of FIG. 73.

Each aseptic coupling 1400 includes an alignment post 1412 and an alignment guide 1416 (e.g., see FIGS. 77 and 78). The alignment guide 1416 defines an internal space configured to slidably receive the alignment post 1412 of another aseptic coupling 1400. When two aseptic couplings 1400 are coupled together to create an aseptic coupling arrangement 1500 (in both/either of the pre-coupled configuration and the coupled configuration), the alignment post 1412 of a first one of the aseptic couplings 1400 is engaged within the alignment guide 1416 of a second one of the aseptic couplings 1400, and the alignment post 1412 of the second one of the aseptic couplings 1400 is engaged within the alignment guide 1416 of the first one of the aseptic couplings 1400.

Each alignment guide 1416 includes one or more flexible latch members 1417 (e.g., see FIGS. 77 and 78). Each alignment post 1412 includes one or more notches 1413 that each receive a latch member 1417 of a mating coupling 1400. In the depicted embodiment, each alignment guide 1416 includes two flexible latch members 1417 and each alignment post 1412 includes two notches 1413.

In the depicted embodiment, the centerlines of the alignment post 1412, the alignment guide 1416, and the central fluid flow path of the main body 1410 are all in a same plane. The central fluid flow path of the main body 1410 is in between the alignment post 1412 and the alignment guide 1416.

To create the aseptic coupling arrangement 1500 shown in FIGS. 86-89, a user engages the alignment posts 1412 with the alignment guides 1416 of two aseptic couplings 1400. The latch members 1417 snap into the notches 1413. This is the pre-coupled configuration. The membranes 1440 are still attached, and are compressed between the face ends of the seals 1430. The user then strips the membranes 1440 off from the front faces of the main bodies 1410. The face ends of the seals 1430 then contact each other. This is the operative, coupled configuration. No further compression between the seals 1430 is needed. The coupling process merely includes snapping two aseptic couplings 1400 into engagement with each other and then removing the membranes 1440. While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:
1. An aseptic fluid coupling comprising:
 a main body defining a longitudinal axis and a bore, the main body comprising:
  a front face;
  a termination that is at an opposite end of the main body in comparison to the front face;
  an alignment post; and
  an alignment guide defining internal space configured to slidably receive an alignment post of another aseptic fluid coupling when two of the aseptic fluid couplings are mated together;
 a seal member having a width along the longitudinal axis between a first end and a second end of the seal member, the seal member including a portion disposed within the bore and a portion extending from the front face around the longitudinal axis; and
 a flexible membrane including a portion attached to the front face around the seal member to block contaminants from entering a fluid flow path, the membrane also including a tail end portion that is at an opposite end of the membrane in comparison to the portion attached to the front face,
 wherein the fluid flow path is defined through the aseptic fluid coupling, wherein a portion of the fluid flow path is defined by the seal member along an entirety of the width of the seal member, wherein the alignment post and the alignment guide each include attachment features whereby the alignment post latches with an engaged alignment guide and the alignment guide latches with an engaged alignment post, and wherein the attachment features of the alignment guide includes at least one flexible latch member.

2. The aseptic fluid coupling of claim 1, wherein the alignment post extends parallel to the longitudinal axis.

3. The aseptic fluid coupling of claim 1, wherein the membrane is porous such that air can pass through the membrane.

4. The aseptic fluid coupling of claim 1, wherein the attachment features of the alignment post includes at least one groove.

5. The aseptic fluid coupling of claim 1, wherein the main body comprises a termination member that includes the termination, and wherein the termination member extends into the bore.

6. The aseptic fluid coupling of claim 5, wherein the termination member snaps into engagement with other portions of the main body.

7. The aseptic fluid coupling of claim 6, wherein the termination member is rotatable about the longitudinal axis in relation to the other portions of the main body.

8. The aseptic fluid coupling of claim 6, further comprising a seal disposed between the termination member and the other portions of the main body.

9. The aseptic fluid coupling of claim 5, wherein the termination member defines a portion of the fluid flow path.

10. The aseptic fluid coupling of claim 5, wherein the termination member abuts against the seal member within the bore.

11. The aseptic fluid coupling of claim 1, further comprising a protective cover that is releasably engageable with the main body.

12. The aseptic fluid coupling of claim 11, wherein the protective cover presses two layers of the membrane against the seal member while the protective cover is engaged with the main body.

13. The aseptic fluid coupling of claim 11, wherein the protective cover defines an opening aligned with the longitudinal axis while the protective cover is engaged with the main body.

* * * * *